United States Patent
Copeland et al.

(10) Patent No.: US 11,998,626 B2
(45) Date of Patent: *Jun. 4, 2024

(54) ALCOHOL CONTAINING NON-ANTIMICROBIAL CLEANSING COMPOSITION

(71) Applicant: GOJO Industries, Inc., Akron, OH (US)

(72) Inventors: Amanda Jo Copeland, Seville, OH (US); Venkatesan Padyachi, Kendall Park, NJ (US); James Bingham, Akron, OH (US); Nick Ciavarella, Seven Hills, OH (US); Kayla Elise Ivey, Cuyahoga Falls, OH (US); Carey Jaros, Shaker Heights, OH (US); Daniel Willis, Clinton, OH (US); Jessica Rae Tittl, Akron, OH (US); Srini Venkatesh, Hudson, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,608

(22) Filed: Apr. 17, 2023

(65) Prior Publication Data
US 2023/0248625 A1    Aug. 10, 2023

Related U.S. Application Data

(63) Continuation of application No. 17/507,862, filed on Oct. 22, 2021, now Pat. No. 11,660,258, which is a (Continued)

(51) Int. Cl.
*C11D 1/02* (2006.01)
*A61K 8/04* (2006.01)
(Continued)

(52) U.S. Cl.
CPC ............... *A61K 8/34* (2013.01); *A61K 8/046* (2013.01); *A61K 8/345* (2013.01); *A61K 8/365* (2013.01);
(Continued)

(58) Field of Classification Search
CPC .... C11D 1/02; C11D 1/29; C11D 1/88; C11D 1/90; C11D 3/2006; C11D 3/48;
(Continued)

(56) References Cited

U.S. PATENT DOCUMENTS

| 5,851,974 A | 12/1998 | Sandhu |
| 6,048,834 A | 4/2000 | Drapier et al. |

(Continued)

FOREIGN PATENT DOCUMENTS

| AU | 669450 B2 | 6/1996 |
| AU | 2005209647 A1 | 10/2005 |

(Continued)

OTHER PUBLICATIONS

International Search Report and Written Opinion from PCT/US2018/030444 dated Jul. 25, 2018 (6 pages).
(Continued)

*Primary Examiner* — Brian P Mruk
(74) *Attorney, Agent, or Firm* — Calfee, Halter & Griswold LLP

(57) ABSTRACT

A non-antimicrobial cleansing composition is disclosed comprising from about 10.0 wt. % to less than about 40 wt. % of one or more $C_1$-$C_8$ alcohols; about 0.5 wt. % to about 10.0 wt. % of at least one primary surfactant; 0 wt. % to about 10.0 wt. % of at least one secondary surfactant, with the primary and secondary surfactants having an HLB value greater than 8; a pH adjusting agent; and water. The composition does not achieve a microbial kill level greater than 2.0 log.

15 Claims, 10 Drawing Sheets

Related U.S. Application Data continuation of application No. 15/968,082, filed on May 1, 2018, now Pat. No. 11,185,483.

(60) Provisional application No. 62/492,622, filed on May 1, 2017, provisional application No. 62/555,986, filed on Sep. 8, 2017, provisional application No. 62/609,487, filed on Dec. 22, 2017.

(51) Int. Cl.

| *A61K 8/34* | (2006.01) |
|---|---|
| *A61K 8/365* | (2006.01) |
| *A61K 8/44* | (2006.01) |
| *A61K 8/46* | (2006.01) |
| *A61Q 17/00* | (2006.01) |
| *A61Q 19/10* | (2006.01) |
| *B08B 3/04* | (2006.01) |
| *C11D 1/29* | (2006.01) |
| *C11D 1/88* | (2006.01) |
| *C11D 1/90* | (2006.01) |
| *C11D 3/48* | (2006.01) |

(52) U.S. Cl.
CPC ............... *A61K 8/44* (2013.01); *A61K 8/442* (2013.01); *A61K 8/463* (2013.01); *A61Q 17/005* (2013.01); *A61Q 19/10* (2013.01); *A61K 2800/30* (2013.01); *A61K 2800/34* (2013.01); *A61K 2800/48* (2013.01); *A61K 2800/596* (2013.01); *A61K 2800/75* (2013.01); *A61K 2800/805* (2013.01)

(58) Field of Classification Search
CPC .......... B08B 3/04; A61Q 19/10; A61K 8/046; A61K 8/34; A61K 8/463; A61K 2800/34
See application file for complete search history.

(56) References Cited

U.S. PATENT DOCUMENTS

| 6,269,817 | B1 | 8/2001 | Nagashima et al. | |
|---|---|---|---|---|
| 6,455,482 | B1 | 9/2002 | D'Ambrogio et al. | |
| 7,348,299 | B2 | 3/2008 | Keenan et al. | |
| 11,185,482 | B2 * | 11/2021 | Padyachi | A61Q 19/10 |
| 11,185,483 | B2 * | 11/2021 | Copeland | A61K 8/44 |
| 11,633,334 | B2 | 4/2023 | Copeland et al. | |
| 11,660,258 | B2 * | 5/2023 | Copeland | A61K 8/34 510/505 |
| 11,712,409 | B2 * | 8/2023 | Padyachi | A61Q 17/005 510/505 |
| 2004/0136943 | A1 | 7/2004 | Tomokuni | |
| 2006/0018853 | A1 | 1/2006 | Watanabe | |
| 2006/0115440 | A1 | 6/2006 | Arata et al. | |
| 2007/0066499 | A1 | 3/2007 | Slavtcheff et al. | |
| 2007/0219107 | A1 | 9/2007 | Nonomura et al. | |
| 2010/0081596 | A1 | 4/2010 | Rong et al. | |
| 2010/0172847 | A1 | 7/2010 | Modak et al. | |
| 2011/0263471 | A1 | 10/2011 | Barnhart et al. | |
| 2012/0295831 | A1 | 11/2012 | Masters et al. | |
| 2013/0172415 | A1 | 7/2013 | Vermeulen et al. | |
| 2013/0295032 | A1 | 11/2013 | Yeung et al. | |
| 2014/0024711 | A1 | 1/2014 | Hedbom et al. | |
| 2014/0135245 | A1 | 5/2014 | Annaheim et al. | |
| 2014/0274863 | A1 | 9/2014 | Trosin et al. | |
| 2015/0250166 | A1 | 9/2015 | Goldblum et al. | |
| 2016/0060416 | A1 | 3/2016 | Fernandez De Castro et al. | |
| 2017/0216191 | A1 | 8/2017 | Deisenroth et al. | |
| 2017/0281497 | A1 | 10/2017 | Kobayashi | |
| 2018/0311127 | A1 | 11/2018 | Padyachi et al. | |
| 2018/0311128 | A1 | 11/2018 | Copeland et al. | |
| 2020/0131454 | A1 | 4/2020 | Copeland et al. | |
| 2021/0071107 | A1 | 3/2021 | Tang et al. | |
| 2022/0062128 | A1 | 3/2022 | Padyachi et al. | |
| 2022/0062137 | A1 | 3/2022 | Copeland et al. | |
| 2022/0079851 | A1 | 3/2022 | Copeland et al. | |

FOREIGN PATENT DOCUMENTS

| CN | 101756803 | A | 6/2010 | |
|---|---|---|---|---|
| CN | 101927004 | A | 12/2010 | |
| CN | 102618398 | A | 8/2012 | |
| CN | 104352390 | * | 2/2015 | ............... A61K 8/97 |
| CN | 104352390 | A | 2/2015 | |
| CN | 107669667 | A | 2/2018 | |
| CN | 108324635 | A | 7/2018 | |
| DE | 4329517 | A1 | 3/1995 | |
| DE | 4444237 | A1 | 6/1996 | |
| JP | 63054311 | A | 3/1988 | |
| JP | 09025223 | A | 1/1997 | |
| JP | 2003073221 | A | 3/2003 | |
| JP | 2009221138 | A | 10/2009 | |
| KR | 1020100078777 | A | 7/2010 | |
| WO | 9606153 | A2 | 2/1996 | |
| WO | 0248298 | A1 | 6/2002 | |
| WO | 2008157847 | A1 | 12/2008 | |
| WO | 2016104692 | A1 | 6/2016 | |

OTHER PUBLICATIONS

International Search Report and Written Opinion from PCT/US2018/030455 dated Jul. 27, 2018 (15 pages).

Mintel;anonymous: "Shampoo for Normal Hair", XP055655438,retrieved from www.gnpd.com Database accession No. 1536766 Abstract, May 17, 2011.

Oh et al., "Antimicrobial activity of ethanol, glycerol monolaurate or lacticacid against Listeria monocytogenes", International Journal of Foodmicrobiology, Elsevier BV, NL, vol. 20, No. 4,Dec. 1, 1993 (Dec. 1, 1993), pp. 239-246.

* cited by examiner

ALCOHOL CONTAINING NON-ANTIMICROBIAL CLEANSING COMPOSITION

RELATED APPLICATIONS

This application is a continuation of U.S. patent application Ser. No. 17/507,862, filed on Oct. 22, 2021 (now U.S. Pat. No. 11,660,258), which is a continuation of U.S. patent application Ser. No. 15/968,082, filed on May 1, 2018, now U.S. Pat. No. 11,185,483, which claims priority to and the benefits of U.S. Provisional Patent Application No. 62/492,622, filed on May 1, 2017, U.S. Provisional Patent Application No. 62/555,986, filed on Sep. 8, 2017, and U.S. Provisional Patent Application No. 62/609,487 filed on Dec. 22, 2017, all of which are incorporated herein in their entirety.

BACKGROUND

Hand wash compositions are preferably formulated to provide good cleaning, good foaming, and to be mild to the skin. Hand wash compositions typically employ a surfactant system to provide cleaning and foaming functionalities. Moisturizers or other skin benefit agents may also be employed to promote overall skin health and wellness.

Alcoholic products are popular as sanitizers for the skin, as high concentrations of alcohol can have antimicrobial properties. However, when placed on the skin, alcohol and other antimicrobial agents can be drying and can cause irritation. Additionally, alcohol is known to have strong de-foaming properties. Thus, when alcohol is added to a hand wash, it is typically believed that skin health, aesthetics, and foam quality may be sacrificed. Therefore, it would be beneficial to design a new non-antimicrobial cleansing composition that contains alcohol without negatively impacting the composition's skin health benefits and/or foaming ability.

Formulating a composition as non-antimicrobial provides additional benefits other than being less prone to irritation. Particularly, often the strength of an antimicrobial composition is not required and less potent options that remove pathogens, rather than kill pathogens, would be sufficient. not necessary needed, less potent options. Minimizing the unnecessary use of antimicrobial agents will help limit the potential development of antimicrobial resistance.

Infections caused by the bacteria *Clostridium difficile* (*C. difficile*) remain at historically high levels. *C. difficile* is a spore-forming, Gram-positive anaerobic bacillus of the human intestine and is thought to be present in 2-5% of the adult population. Pathogenic *C. difficile* strains produce multiple toxins, the most well-characterized of which are enterotoxin (*Clostridium difficile* toxin A) and cytotoxin (*C. difficile* toxin B), both of which can produce diarrhea and inflammation in infected patients. The emergence of a new, highly toxic strain of *C. difficile*, resistant to fluoroquinolone antibiotics, such as ciprofloxacin and levofloxacin have also been reported.

A variety of strategies have been proposed to kill *C. difficile* spores on various surfaces, with limited success. Until now, alcohol-based sanitizers have not generally been effective in killing or removing *C. difficile* spores. In fact, ethanol is sometimes used to store *C. difficile* spores.

SUMMARY

Various aspects of the present inventive concepts are directed to a non-antimicrobial cleansing composition comprising from 10.0 wt. % to less than 30 wt. % of one or more $C_1$-$C_8$ alcohols; 0.5 wt. % to about 10.0 wt. % of at least one primary surfactant; 0 wt. % to about 10.0 wt. % of at least one secondary surfactant, wherein the primary and secondary surfactants have an HLB value greater than 8; a pH adjusting agent; and water. The non-antimicrobial composition does not achieve a microbial kill level greater than 2.0 log.

In some exemplary embodiments, the composition does not achieve a microbial kill level greater than 1.5 log.

In some exemplary embodiments, the composition removes at least 98% of pathogens from a surface.

The one or more $C_1$-$C_8$ alcohols may be selected from the group consisting of methanol, ethanol, isopropanol, butanol, pentanol, hexanol, and isomers and mixtures thereof. In some exemplary embodiments, the composition includes less than 25 wt. % of one or more $C_1$-$C_8$ alcohols.

The primary surfactant may be an anionic surfactant selected from the group consisting of sodium alkyl sulfate, sodium dodecyl sulfate, sodium dodecylbenzene sulfonate, sodium laurate, sodium laureth sulfate, sodium lauryl sarcosinate, potassium lauryl sulfate, ammonium lauryl sulfate, ammonium laureth sulfate, ammonium xylene sulfonate, magnesium laureth sulfate, and sodium myreth sulfate, sodium nonanoyloxybenzenesulfonate, carboxylates, sulphated esters, sulphated alkanolamides, alkylphenols, and mixtures thereof.

In some exemplary embodiments, the primary surfactant comprises sodium laureth sulfate and the secondary surfactant comprises at least one zwitterionic surfactant.

The zwitterionic surfactant may comprise one or more of cocamidopropyl betaine, cocamidopropyl hydroxyl sultaine, lauramidopropyl hydroxyl sultaine, lauramine oxide, myristamine oxide, disodium lauroamphodiacetate, disodium cocoamphodiacetate, sodium lauroamphoacetate, sodium cocoamphoacetate, disodium cocoamphodipropionate, disodium lauroamphodipropionate, and mixtures thereof.

The non-antimicrobial cleansing composition may further comprise from 0.01 wt. % to 5.0 wt. % of one or more humectants, based on the total weight of the composition, wherein the humectant is selected from the group consisting of propylene glycol, hexylene glycol, 1,4-dihydroxyhexane, 1,2,6-hexanetriol, sorbitol, butylene glycol, caprylyl glycol, methyl propane diol, dipropylene glycol, triethylene glycol, glycerin (glycerol), polyethylene glycol, ethoxydiglycol, polyethylene sorbitol, and combinations thereof.

Some exemplary embodiments of the non-antimicrobial cleansing composition include less than 3 wt. % of an oil, based on a total weight of the cleansing composition.

Further exemplary aspects of the present inventive concepts are directed to a method of cleansing a surface that includes applying a non-antimicrobial cleansing composition to a surface, wherein the cleansing composition comprises from 10.0 wt. % to less than 30 wt. % of one or more $C_1$-$C_8$ alcohols; 0.5 wt. % to about 10.0 wt. % of at least one primary surfactant; 0 wt. % to about 10.0 wt. % of at least one secondary surfactant, wherein the primary and secondary surfactants have an HLB value greater than 8; a pH adjusting agent; and water, the aforementioned amounts being based on the total weight of the non-antimicrobial composition. The composition does not achieve a microbial kill level greater than 2.0 log.

Further exemplary embodiments of the present inventive concepts are directed to a non-antimicrobial cleansing composition comprising: from about 10.0 wt. % to less than about 25 wt. % of one or more $C_1$-$C_8$ alcohols based on the total weight of the composition; about 3.0 wt. % to about 10.0 wt. % of at least one fatty acid, based on a total weight of the cleansing composition; about 0.5 wt. % to about 5.0 wt. % of at least one humectant, based on a total weight of the cleansing composition; less than about 3.0 wt. % of an oil, based on a total weight of the cleansing composition; a basic pH adjusting agent; and water.

Yet further exemplary embodiments of the present inventive concepts are directed to a non-antimicrobial cleansing composition comprising from about 10.0 wt. % to less than about 30 wt. % of one or more $C_1$-$C_8$ alcohols; a surfactant system comprising about 0.5 wt. % to about 10.0 wt. % of at least one primary surfactant and 0 wt. % to about 10.0 wt. % of at least one secondary surfactant, wherein the primary and secondary surfactants have an HLB value greater than 8; and water, the aforementioned amounts being based on the total weight of the non-antimicrobial composition. The cleansing composition does not achieve a microbial kill level greater than 3.0 log. Additionally, the cleansing composition achieves an interfacial tension when applied to a skin surface of at least 2 times lower than the interfacial tension of an otherwise identical composition that includes less than 10 wt. % alcohol.

Yet further exemplary embodiments of the present inventive concepts are directed to a non-antimicrobial cleansing solution comprising from about 15.0 wt. % to less than 25 wt. % of one or more $C_1$-$C_8$ alcohols; a surfactant system comprising about 2.5 wt. % to about 10.0 wt. % of at least one primary surfactant and about 2 wt. % to about 10.0 wt. % of at least one secondary surfactant; a pH adjusting agent; and water, the aforementioned amounts being based on the total weight of the non-antimicrobial composition. In some exemplary embodiments, the composition is a single-phase composition and does not achieve a microbial kill level greater than 3.0 log.

Further exemplary embodiments of the present inventive concepts are directed to a non-antimicrobial cleansing composition comprising: from about 10.0 wt. % to less than about 25 wt. % of one or more $C_1$-$C_8$ alcohols; about 0.5 wt. % to about 10.0 wt. % of at least one primary surfactant; 0 wt. % to about 10.0 wt. % of at least one secondary surfactant wherein the primary and secondary surfactants have an HLB value greater than 8; and water, the aforementioned amounts being based on the total weight of the non-antimicrobial composition. The non-antimicrobial composition does not achieve a microbial kill level greater than 2.0 log. Additionally, when applied to a surface contaminated with *C. difficile* spores, the composition achieves at least a 94.0% reduction in *C. difficile* spores.

Numerous other aspects, advantages, and/or features of the general inventive concepts will become more readily apparent from the following detailed description of exemplary embodiments and from the accompanying drawings being submitted herewith.

DETAILED DESCRIPTION

Figure 1:
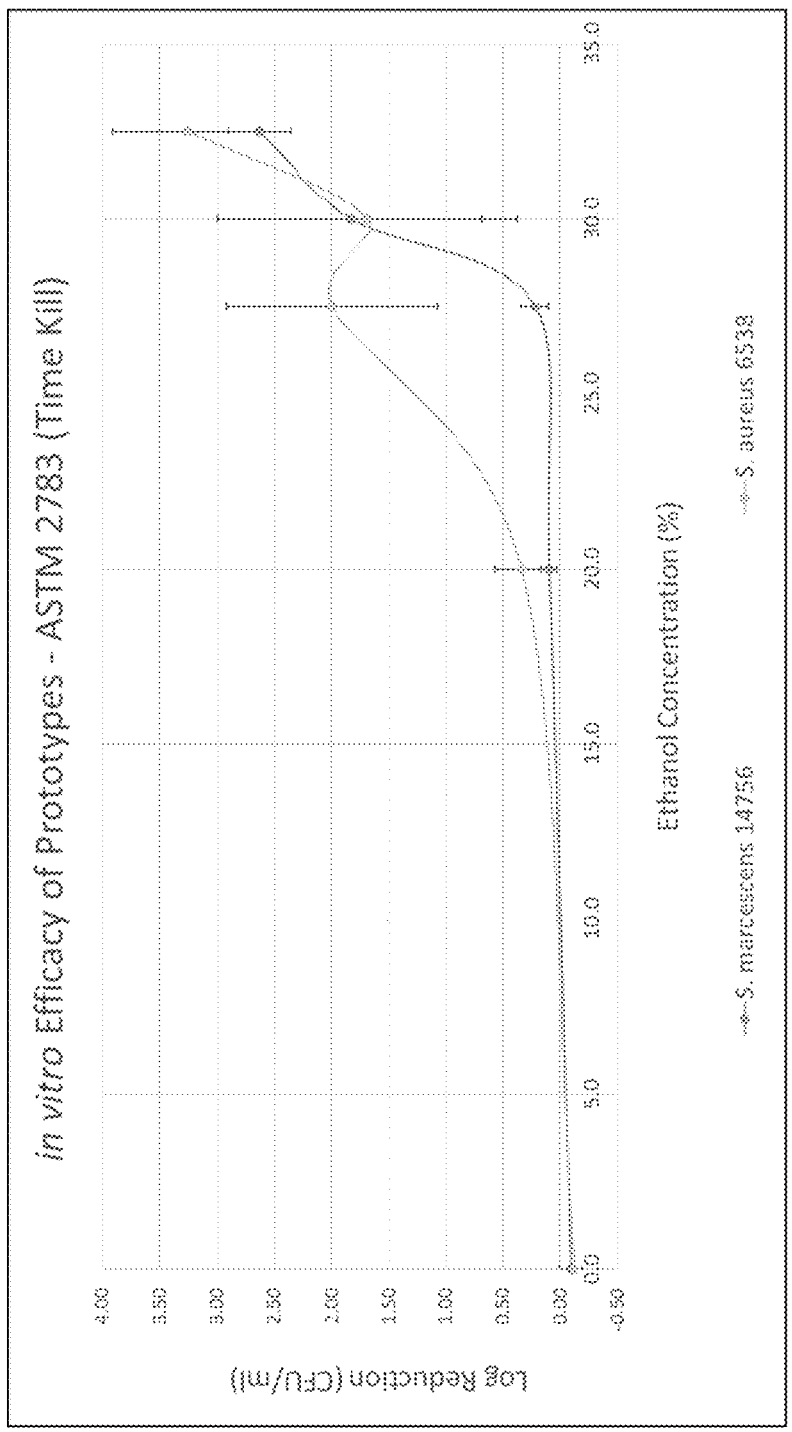
FIG. 1 graphically illustrates the in vitro efficacy (time kill) of the non-antimicrobial cleansing composition using various concentrations of ethanol.

Unless otherwise defined, all technical and scientific terms used herein have the same meaning as commonly understood by one of ordinary skill in the art to which this application pertains. Although other methods and materials similar or equivalent to those described herein may be used in the practice or testing of the exemplary embodiments, exemplary suitable methods and materials are described below. In case of conflict, the present specification, including definitions, will control. In addition, the materials, methods, and examples are illustrative only and are not intended to be limiting of the general inventive concepts.

The terminology as set forth herein is for description of the exemplary embodiments only and should not be construed as limiting the application as a whole. Unless otherwise specified, "a," "an," "the," and "at least one" are used interchangeably. Furthermore, as used in the description of the application and the appended claims, the singular forms "a," "an," and "the" are inclusive of their plural forms, unless contradicted by the surrounding context.

Unless otherwise indicated, all numbers expressing quantities of ingredients, chemical and molecular properties, reaction conditions, and so forth used in the specification and claims are to be understood as being modified in all instances by the term "about." The term "about" means within +/−10% of a value, or more preferably, within +/−5% of a value, and most preferably within +/−1% of a value.

Accordingly, unless indicated to the contrary, the numerical parameters set forth in the specification and attached claims are approximations that may vary depending upon the desired properties sought to be obtained by the present exemplary embodiments. At the very least each numerical parameter should be construed in light of the number of significant digits and ordinary rounding approaches.

Every numerical range given throughout this specification and claims will include every narrower numerical range that falls within such broader numerical range, as if such narrower numerical ranges were all expressly written herein.

The phrase "topical composition" means a composition suitable for application directly to a surface, such as the surface of a human or animal body, including skin, and/or other surfaces, such as hair and nails. The topical composition may further be applied to an inanimate surface, such as a table, counter, floor, food, utensil, appliance, object, and the like.

The term "non-antimicrobial composition" means a composition that achieves a microbial kill less than 2.0 log, including less than 1.5 log, less than 1.0 log, and less than 0.5 log, during use. The term "non-antimicrobial composition" includes non-antibacterial compositions, non-antiviral compositions, non-antifungal compositions and non-antiparasitic compositions. In accordance with the present inventive concepts, as defined herein, a non-antimicrobial composition achieves a microbial removal level of 3.0 log or less, including 2.5 log or less, 2.0 log or less, and no greater than 1.5 log, during use.

It has now been discovered that it is possible to formulate a non-antimicrobial topical cleansing composition, particularly a liquid or foaming hand soap and/or concentrate thereof, that has a proper balance of ingredients for providing a high cleansing ability, high foam, and good skin conditioning, while including alcohol.

Accordingly, the present disclosure relates to a non-antimicrobial cleansing composition that includes at least one $C_1$-$C_8$ alcohol and a method of using the same. Conventionally, it was believed that the addition of alcohol to a soap composition would negatively impact skin health and reduce the soap's foam quality. However, it has been discovered that incorporating at least one $C_1$-$C_8$ alcohol in the cleansing composition disclosed herein, provides numerous benefits to the cleansing composition, such as superior efficacy, clean release functionality, and self-preservation, while maintaining good skin health benefits and foam quality and stability. By "foam stability" is meant the length of time that it takes for a foam to break down into a liquid.

The concept of "clean release" encompasses the ability to achieve better pathogen and soil removal on both healthy and dry/irritated skin, due at least in part to the composition's improved spreadability and wettability. The clean release functionality also provides for a faster rinse, which in turn conserves water compared to traditional commercial soap.

Additionally, various embodiments of the topical cleansing composition are substantially free of harsh preservatives, parabens, phthalates, further anti-microbial, and antibacterial ingredients. In some exemplary embodiments, the cleansing composition includes less than 2.0 wt. %, less than 1.0 wt. %, less than 0.5 wt. %, or less than 0.1 wt. % of harsh preservatives, parabens, phthalates, further antimicrobial, and antibacterial ingredients. In some exemplary embodiments, the cleansing composition is devoid of such ingredients. In various exemplary embodiments, the cleansing composition comprises at least 75% bio-based ingredients, or at least 85% bio-based ingredients, or at least 90% bio-based ingredients. In certain exemplary embodiments, the topical cleansing composition is used for application to the skin and may be in the form of a liquid or foamable skin cleanser, a wipe, a concentrate, a lotion, and other forms desirable for a cleansing composition. The topical cleansing composition may be applied to the skin before, during, or after skin cleaning.

The non-antimicrobial cleansing composition may be provided as an aqueous solution or emulsion. In some exemplary embodiments, the cleansing composition is a single-phase solution, meaning that it is free of additional phases, such as an oil phase.

The non-antimicrobial cleansing composition of the present disclosure includes at least 5.0 wt. % of one or more $C_1$-$C_8$ alcohols, based on the total weight of the non-antimicrobial cleansing composition, including without limitation, at least 10.0 wt. %, or at least 15.0 wt. %, or at least 18.0 wt. %, or at least 19.0 wt. % or at least 20.0 wt. %. In some exemplary embodiments, the non-antimicrobial cleansing composition includes no greater than 35.0 wt. % of a $C_1$-$C_8$ alcohol, based on the total weight of the non-antimicrobial cleansing composition, including, without limitation, no greater than 30.0 wt. %, or no greater than 28.0 wt. %, or no greater than 27.0 wt. %, or no greater than 25.0 wt. %, or no greater than 22.0 wt. %. In some exemplary embodiments, the non-antimicrobial cleansing composition includes from about 5.0 wt. % to about 30 wt. % of one or more $C_1$-$C_8$ alcohols, based on the total weight of the composition, including without limitation, about 8.0 wt. % to about 28.0 wt. %, about 10.0 wt. % to about 27.0 wt. %, about 12.0 wt. % to about 25.0 wt. %, about 15.0 wt. % to about 22.0 wt. %, about 18.0 wt. % to about 21 wt. %, and every narrower numerical range that falls within the broader ranges.

In some exemplary embodiments, the one or more $C_1$-$C_8$ alcohol is included at a concentration less than a concentration that would provide antimicrobial efficacy. For instance, the $C_1$-$C_8$ alcohol may be present in any concentration below a concentration that would cause the composition to achieve a microbial kill of greater than 3 log, or greater than 2 log.

The alcohol is a $C_1$-$C_8$ alcohol, i.e. an alcohol containing 1 to 8 carbon atoms. Such alcohols may be referred to as lower alkanols. Examples of lower alkanols include, but are not limited to, methanol, ethanol, propanol, butanol, pentanol, hexanol, heptanol, octanol, and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the cleansing composition comprises a mixture of alcohols. In one or more embodiments, the non-antimicrobial cleansing composition comprises a mixture of ethanol and isopropanol. In one or more embodiments, the non-antimicrobial cleansing composition comprises a mixture of isopropanol and n-propanol.

In some exemplary embodiments, the alcohol component may be substituted by any hydrotrope capable of providing a function similar to a $C_1$-$C_8$ alcohol. Suitable hydrotropes include, for example, $C_2$-$C_8$ hydrotropes, such as $C_2$-$C_6$ polyols and glycols including butylene glycol, propylene glycol, ethylene glycol, and other such polyols and glycols. In various exemplary embodiments, the non-antimicrobial composition includes a mixture of an alcohol and one or more hydrotropes.

In certain exemplary embodiments, the non-antimicrobial cleansing composition includes water in an amount quantum sufficit (q.s.). In certain exemplary embodiments, the non-antimicrobial composition comprises at least about 1.0 wt. % water, in another embodiment the non-antimicrobial cleansing composition comprises at least about 30.0 wt. % water, in another embodiment, the non-antimicrobial cleansing composition comprises at least about 40.0 wt. % water, in another embodiment, the non-antimicrobial cleansing composition comprises at least about 50.0 wt. % water, in another embodiment, the non-antimicrobial cleansing composition comprises at least about 60.0 wt. % water, in another embodiment, the non-antimicrobial cleansing composition comprises at least about 70.0 wt. % water, and in yet another embodiment, the non-antimicrobial cleansing composition comprises at least about 80.0 wt. % water. In other embodiments, the non-antimicrobial composition comprises from about 50.0 wt. % to about 95.0 wt. % water. In yet other embodiments, the non-antimicrobial composition comprises from about 65.0 to about 90.0 wt. % water, or from about 75.0 wt. % to about 85.0 wt. % water. More or less water may be required in certain instances, depending particularly on other ingredients and/or the amounts thereof employed in the non-antimicrobial composition.

The non-antimicrobial cleansing composition may include multiple surfactants utilized in a synergistic relationship in amounts ranging up to about 40.0 wt. %. It will be appreciated by one skilled in the art that in one or more embodiments, a surfactant system may be chosen to enhance the germ removal effect of the non-antimicrobial cleansing composition. Such a surfactant system may include at least one primary surfactant and at least one secondary surfactant. The surfactant system boosts soap performance and works synergistically with the alcohol to provide "clean-release" functionality. As mentioned above, clean release functionality allows the soap to penetrate deeper into skin's cracks and crevices to gently remove more pathogens and soil than otherwise comparable soap that does not include the synergistic alcohol and surfactant system. This is particularly useful for dry/irritated skin, where cracks and crevices are more prevalent. In some exemplary embodiments, the clean-release functionality provided by the surfactant system removes at least 10% more soil and pathogens than regular soap, including at least 15%, at least 20%, at least 25%, and at least 30% more soil and pathogens than otherwise comparable soap that does not include the synergistic alcohol and surfactant system.

The primary surfactant may comprise any of an anionic, nonionic, cationic, zwitterionic, fatty acid surfactant. In some exemplary embodiments, the primary surfactant is an anionic surfactant in an amount no greater than 30 wt. %, based on the total weight of the non-antimicrobial composition. In some exemplary embodiments, the non-antimicrobial cleansing composition comprises about 0.5 wt. % to about 10.0 wt. % of an anionic surfactant, or about 1.0 wt. % to about 8.0 wt. % of an anionic surfactant, or about 2.0 wt. % to about 5.0 wt. % of an anionic surfactant, or about 2.2 wt. % to about 4.0 wt. % of an anionic surfactant. Exemplary anionic surfactants include sulfates, such as sodium alkyl sulfate, sodium dodecyl sulfate, sodium dodecylbenzenesulfonate, sodium laurate, sodium laureth sulfate, sodium lauryl sarcosinate, potassium lauryl sulfate, ammonium lauryl sulfate, ammonium laureth sulfate, ammonium xylene sulfonate, magnesium laureth sulfate, and sodium myreth sulfate; sulfonates, such as sodium nonanoyloxybenzenesulfonate; carboxylates; sulphated esters; sulphated alkanolamides; alkylphenols; and mixtures thereof. In some exemplary embodiments, the primary surfactant comprises any one or more of sodium laureth sulfate, ammonium lauryl sulfate, ammonium laureth sulfate, ammonium xylene sulfonate. In some exemplary embodiments, the cleansing composition is free of anionic surfactants.

In some exemplary embodiments, the non-antimicrobial cleansing composition comprises at least one secondary surfactant. The secondary surfactant may be included in an amount no greater than 10 wt. %, based on the total weight of the non-antimicrobial cleansing composition. In some exemplary embodiments, the secondary surfactant is included in an amount from about 0.01 wt. % to about 10.0 wt. %, or about 0.5 wt. % to about 8.0 wt. %, or about 0.7 wt. % to about 5.0 wt. %, or about 1.0 wt. % to about 2.5 wt. %.

The secondary surfactant may comprise one or more of a zwitterionic (or amphoteric) surfactant, non-ionic surfactant, cationic surfactant, or anionic surfactant. Zwitterionic (amphoteric) surfactants have both cationic and anionic centers attached to the same molecule. Zwitterionic may be either anionic, cationic or no-ionic depending on the pH level of the aqueous solution.

Exemplary zwitterionic surfactants include betaines, such as cocamidopropyl betaine; sultaines, such as cocamidopropyl hydroxyl sultaine and lauramidopropyl hydroxyl sultaine; and amphoacetates and amphodiacetates, such as disodium lauroamphodiacetate, disodium cocoamphodiacetate, sodium lauroamphoacetate, sodium cocoamphoacetate, disodium cocoamphodipropionate and disodium lauroamphodipropionate. In some exemplary embodiments, the zwitterionic surfactant is cocamide monoethananolamine.

Exemplary nonionic surfactants include fatty alcohols such as cetyl alcohol, stearyl alcohol, cetostearyl alcohol, and oleyl alcohol, polyoxamers, ethoxylated fatty alcohols, such as PEG-80 sorbitan laurate, polyoxyethylene glycol alkyl ethers, such as octaethylene glycol monododecyl ether, and pentaethylene glycol monododecyl ether, polyoxypropylene glycol alkyl ethers, glucoside alkyl ethers, polyoxyethylene glycol octylphenol ethers, polyoxyethylene glycol alkylphenol ethers, such as nonoxynol-9, glycerol alkyl esters such as glyceryl laurate, polyoxyethylene glycol sorbitan alkyl esters, such as polysorbate, sorbitan alkyl esters, cocamide MEA, cocamide DEA, amine oxides, such as dodecyldimethylamine oxide, block copolymers of polyethylene glycol and polypropylene glycol, such as poloxamers, polyethoxylated tallow amine, and mixtures thereof.

Exemplary cationic surfactants include quaternary ammonium salts, linear alkyl-amines, and alkyl ammoniums.

Auxiliary surfactants may be included in the non-antimicrobial cleansing compositions for the purpose of boosting or modifying the foam quality and characteristics, for modifying the feel of the final formulation during rub in and/or dry time, for providing persistence or long-lasting microbial action of the alcohol, for solubilizing other ingredients such as fragrances or sunscreens, and for irritation mitigation. Auxiliary surfactants include, but are not necessarily limited to, sulfosuccinates, amine oxides, PEG-80 sorbitan laurate, lauric acid, polyglucosides, alkanolamides, sorbitan derivatives, fatty alcohol ethoxylates, quaternary ammonium compounds, amidoamines, sultaines, isothionates, sarcosinates, betaines, and fatty alcohol polyethylene glycols.

Certain exemplary embodiments of the present cleansing composition are free of surfactants that comprise sulphate salts with amine-containing counter ions.

In certain exemplary embodiments, the non-antimicrobial cleansing composition includes one or more humectants. Non-limiting examples of humectants include propylene glycol, hexylene glycol, 1,4-dihydroxyhexane, 1,2,6-hexanetriol, sorbitol, butylene glycol, caprylyl glycol, glyceryl caprylate/caprate, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, Jojoba wax PEG-120 esters (commercially available from FloraTech), hydroxyethyl urea, alpha-hydroxy acids, such as lactic acid, sodium pyrrolidone carboxylic acid, hyaluronic acid, chitin, and the like. In one exemplary embodiment, the humectant is a mixture of glycerin, sodium L-pyroglutamate (Sodium PCA), and polyethylene glycol.

Non-limiting examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

The humectant, or mixture of humectants, may be included in the non-antimicrobial cleansing composition in an amount up to about 20.0 wt. %, or up to about 15.0 wt. %, or up to about 12.0 wt. %, or up to about 10.0 wt. %, or up to about 8.0 wt. % or up to about 8.0 wt. %, or up to about 3.0 wt. %. In certain exemplary embodiments, the humectant is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based upon the total weight of the composition. In one exemplary embodiment, the humectant, or mixture of humectants, is included in an amount from about 0.01 to about 5.0 wt. %, about 0.05 to about 4.0 wt. %, or from about 0.5 to about 3.0 wt. %, based upon the total weight of the composition.

The non-antimicrobial cleansing compositions of the present disclosure exhibit a pH in the range of from about 2.5 to about 12.0, or a pH in the range of from about 3.5 to about 10, or in the range of from about 4.0 and about 9.5. When necessary, a pH adjusting agent or constituent may be used to provide and/or maintain the pH of a composition. Exemplary pH adjusting agents include, but are not limited to, primary amines, such as monoethanolamine; organic acids, such as citric acid, lactic acid, formic acid, acetic acid, proponic acid, butyric acid, caproic acid, oxalic acid, maleic acid, benzoic acid, carbonic acid, and the like. In certain exemplary embodiments, the non-antimicrobial cleansing composition includes citric acid. The pH adjusting agent may be included in any amount necessary to sufficiently adjust the pH to a desired level. In some exemplary embodiments, the pH adjusting agent, if present, is included in at least 0.01 wt. %, or in at least 0.025 wt. %, or in at least 0.05 wt. %, or in at least 0.1 wt. %, or in at least 0.2 wt. %, based on the total weight of the non-antimicrobial cleansing composition. In some exemplary embodiments, the pH adjusting agent is included in an amount between 0.01 wt. % and 1.0 wt. %, or between 0.25 wt. % and 0.5 wt. %, or between 0.05 wt. % and 0.2 wt. %, based on the total weight of the non-antimicrobial cleansing composition.

In one or more embodiments, the non-antimicrobial cleansing composition includes one or more emollients (also known as a skin conditioner or moisturizer). Non-limiting examples of suitable emollients include aloe, aloe oil, jojoba oil, vitamin E, vitamin E acetate (tocopheryl acetate), Vitamin B3 (niacinamide), $C_{8-10}$ alkane diols, sodium salt of pyroglutamic acid (sodium PCA), PEG-7 glyceryl cocoate, coco-glucoside and/or glyceryl oleate (Lamisoft® PO), and polyquaternium, such as polyquaternium 10 and 39.

The emollient can be included in the non-antimicrobial cleansing composition in an amount from about 0.001 to about 5.0 wt. %, in other embodiments, from about 0.005 to about 3.5 wt. %, or from about 0.01 to about 3.0 wt. %, or from about 0.05 to about 2.5 wt. %, or from about 0.1 to about 2.0 wt. %, or from about 0.25 to about 1.5 wt. %, based upon the total weight of the composition.

In some exemplary embodiments, the non-antimicrobial cleansing composition includes less than 3 wt. % of an oil, including less than 2 wt. %, less than 1.5 wt. %, and less than 1.0 wt. %. In some instances, the cleansing composition is substantially (less than 0.5 wt. %) or completely free of oil.

The non-antimicrobial composition may further comprise one or more deposition enhancers. A suitable deposition enhancer works unidirectionally and will allow ingredients within the non-antimicrobial composition to penetrate deeper into the stratum corneum while preventing the loss of materials from the skin. Advantageously, the deposition enhancer provides a cosmetically acceptable skin feel to the formulation.

In one or more embodiments, the deposition enhancers include one or more of surfactants, bile salts and derivatives thereof, chelating agents, and sulphoxides.

Some examples of acceptable deposition enhancers include a quaternary ammonium compound, hydroxypropyl methylcellulose, dimethyl sulphoxides (DMSO), DMA, DMF, 1-dodecylazacycloheptan-2-one (azone), pyrrolidones such as 2-Pyrrolidone (2P) and N-Methyl-2-Pyrrolidone (NMP), long-chain fatty acids such as oleic acid and fatty acids with a saturated alkyl chain length of about $C_{10}$-$C_{12}$ such as lauric acid, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, and lecithin. In one or more exemplary embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer.

In one or more exemplary embodiments, the deposition enhancer is a quaternary ammonium compound such as polyquaternium-6, -7, -10, -22, -37, -39, -74 or -101.

The deposition enhancer may be included in the non-antimicrobial cleansing composition in an amount from about 0.005 wt. % to about 10.0 wt. %, from about 0.01 wt. % to about 5.0 wt. %, from about 0.05 wt. % to about 3.0 wt. %, from about 0.1 wt. % to about 2.0 wt. %, or from about 0.2 wt. % to about 1.0 wt. %, based upon the total weight of the composition.

Optionally, the non-antimicrobial cleansing composition may include one or more chelators. Examples of chelators include ethylenediaminetetraacetic acid (EDTA), and ethylenediamine N,N'-disuccinic acid (EDDS), such as trisodium ethylenediamine disuccinate. In one or more embodiments, the amount of chelating agent is from about 0.05 to about 5 wt. %, in other embodiments, from about 0.1 to about 1 wt. %, or from about 0.2 to about 0.5 wt. % based upon the total weight of the non-antimicrobial cleansing composition.

Although the alcohol in the present composition acts as a preservative, the non-antimicrobial composition may further comprise one or more additional preservatives. A preservative is a natural or synthetic ingredient that can be added to personal care products to prevent spoilage, such as from microbial growth or undesirable chemical changes. As opposed to antimicrobial functionality, which kills or inhibits microbe growth during use of a cleansing composition, a preservative inhibits microbe growth during storage of the composition. Typical cosmetic preservatives are classified as natural antimicrobials, broad-spectrum preservatives, or stabilizers.

Many different types of preservatives are envisioned as being applicable in the current non-antimicrobial composition. Non-limiting examples of preservatives include one or more of isothiazolinones, such as methylchloroisothiazolinone (such as Kathon™ CG) and methylisothiazolinone; parabens including butylparaben, propylparaben, methylparaben and germaben II; phenoxyetyhanol and ethylhexylglycerin, organic acids such as potassium sorbate, sodium benzoate and levulinic acid; and phenoxyethanols. In other exemplary embodiments, the non-antimicrobial cleaning composition is free of any preservative other than alcohol.

The preservative can be added in the non-antimicrobial composition in an amount up to about 10.0 wt. %, or from about 0.05 wt. % to about 5.0 wt. %, or from about 0.08 wt. % to about 2.0 wt. %, based on the weight of the total composition. In one exemplary embodiment, the preservative is present in an amount from about 0.05 to about 0.15 wt. %, based on the weight of the total composition.

The non-antimicrobial composition may further comprise one or more anti-irritants. Anti-irritants reduce signs of inflammation on the skin such as swelling, tenderness, pain, itching, or redness. There are three main types of anti-irritants, all of which are envisioned as being applicable in the subject invention: (1) compounds that operate by complexing the irritant itself, (2) compounds that react with the skin to block reactive sites preventing the irritant from reacting directly with the skin, and (3) compounds that prevent physical contact between the skin and irritant.

Certain exemplary examples of suitable anti-irritants include Aloe Vera, allantoin, anion-cation complexes, aryloxypropionates, azulene, carboxymethyl cellulose, cetyl alcohol, diethyl phthalate, Emcol E607, monoethanolamine, glycogen, lanolin, N-(2-Hydroxylthyl) Palmitamide, N-Lauroyl Sarcosinates, Maypon 4C, mineral oils, miranols, Myristyl lactate, polypropylene glycol, polyvinyl pyrrolidone (PVP), tertiary amine oxides, thiodioglycolic acid, and zirconia. In one exemplary embodiment, the anti-irritant is avenanthrmides (*Avena sativa* (oat), kernel oil, and glycerin) and niacinamide.

The anti-irritant may be included in the non-antimicrobial composition in an amount up to about 10.0 wt. %, in other embodiments, from about 0.005 wt. % to about 3.0 wt. %, and in other embodiments, from about 0.01 wt. % to about 1.0 wt. %, based upon the total weight of the composition.

The non-antimicrobial composition may further comprise a fragrance. Any scent may be used in the non-antimicrobial composition including, but not limited to, any scent classification on a standard fragrance chart, such as floral, oriental, woody, and fresh. Exemplary scents include pomegranate, cinnamon, clove, lavender, peppermint, rosemary, thyme, thieves, lemon, citrus, coconut, apricot, plum, watermelon, ginger and combinations thereof.

The fragrance can be included in the non-antimicrobial composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based upon the total weight of the composition. The fragrance can be any made of any perfume, essential oil, aroma compounds, fixatives, terpenes, solvents, and the like. In certain exemplary embodiments, the essential oils may include, for example, one or more of Limonene, Citrus Aurantium Dulcis (Orange) Peel Oil, Eucalyptus Globulus Leaf Oil, Citrus Grandis (Grapefruit) Peel Oil, Linalool, Litsea Cubeba Fruit Oil, Lavandula Hybrida Oil, Abies Sibirica Oil, Mentha Citrata Leaf Extract, Coriandrum Sativum (Coriander) Fruit Oil, Piper Nigrum (Pepper) Fruit Oil, Vaccinium Angustifolium, Punica Granatum Extract, and Canarium Luzonicum Gum Nonvolatiles.

In certain embodiments, the non-antimicrobial cleansing composition includes one or more UV stabilizers or antioxidants, such as, for example, inorganic sulfite salts, including sodium sulfite, potassium sulfite, ammonium sulfite, sodium bisulfite, ammonium bisulfite, sodium metabisulfite and potassium metabisulfite; diethylhexyl syringylidene malonate; Vitamin A and related compounds, Vitamin E and related compounds; Vitamin C and related compounds; diisopropyl vanillidene malonate (also referred to as DIPVM) and related compounds; Tetrahydrocurcumenoids; green tea, white tea, alpha lipoic acid, isoflavones, selenium, zinc, Coenzyme Q10, turmeric, curcumin, butylhydroxy toluene (BHT), ethylenediaminetetraacetic acid (EDTA), ethylenediamine-N,N'-disuccinic acid (EDDS), and other antioxidants commonly used in the art. Amounts of antioxidants to be added to the compositions of the invention are generally between about 0.01% by weight to about 10.0% by weight, preferably between about 0.1% by weight to about 5.0% by weight.

In certain embodiments, the non-antimicrobial cleansing composition is at least substantially free of dimethicone. By "substantially free" of dimethicone, it is meant that the non-antimicrobial cleansing composition includes less than 5.0 wt. % of dimethicone, or in some exemplary embodiments, less than 1.0 wt. % of dimethicone, or in some exemplary embodiments, less than 0.05 wt. % dimethicone. In various exemplary embodiments, the non-antimicrobial cleansing composition is entirely free of dimethicone.

Some exemplary embodiments include dimethicone, as a skin conditioner. In such embodiments, the dimethicone may be included in at least 0.05 wt. %, or at least 0.1 wt. %, or at least 0.5 wt. %, or at least 0.75 wt. %. In some exemplary embodiments, the non-antimicrobial cleansing composition includes dimethicone in an amount from about 0.1 to 1.0 wt. %, or from 0.5 to 1.0 wt. %.

Examples of dimethicones include silicone glycols, including without limitation dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG-23/PPG-6 dimethicone, PEG-20/PPG-23 dimethicone, PEG 17 dimethicone, PEG-5/PPG-3 methicone, bis-PEG-18 methyl ether dimethyl silane, bis-PEG-20 dimethicone, PEG/PPG-20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof. Advantageously, the non-antimicrobial cleansing composition of these embodiments produces a stable foam when mixed with air, and does not require a foam stabilizer. For purposes of this specification, a stable foam is one that maintains a measurable height for at least about 5 seconds following creation of the foam. Thus, by "foam stability" is meant the length of time that it takes for a foam to break down into a liquid.

Optionally, one or more foam stabilizers may be employed. Thus, in certain embodiments, the alcoholic composition of the present invention further includes at least one foam stabilizer. The foam stabilizer may be polymeric or non-polymeric. In one embodiment, the foam stabilizer may be selected from polymeric or oligomeric foam stabilizers. In one embodiment, the foam stabilizer comprises a cationic oligomer or polymer.

Polymeric foam stabilizers include, for example, polyquatemium polymers. In general, a polyquaternium polymer is one that is designated as such by the CTFA. Polyquatemium polymers may be characterized by containing a quaternary ammonium group.

In one or more embodiments, the polyquatemium polymer includes a quatemized copolymer of vinylpyrrolidone and dimethylamino methacrylate, a hydrophobically modified quaternized copolymer of vinylpyrrolidone & dimethylaminopropyl methacrylamide, or a mixture thereof.

In some exemplary embodiments, the polyquaternium polymer has a molecular weight of from 1,000 to 5,000,000, in another embodiment, from about 1500 to about 2,500,000 and in yet another embodiment, from about 1,000,000 to about 2,000,000.

Other foam stabilizers that may operate to improve foam quality and/or stability include terpolymers of vinylcaprolactam (VCL), vinylpyrrolidone (VP) and dialkylaminoalkyl acrylate, including a VP/vinylcaprolactam/dimethylaminopropyl methacrylamide copolymer. Yet another foam stabilizer includes isobutylene/dimethylaminopropyl maleimide/ ethoxylated maleimide/maleic acid copolymer. These and other foam stabilizers are sometimes referred to as film-forming polymers.

Still other foam stabilizers include acrylamide/ammonium acrylate copolymer, acrylamides/DMAPA acrylates/methoxy PEG methacrylate copolymer, acrylamide/sodium acryloyldimethyltaurate/acrylic acid copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/ethylamine oxide methacrylate copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/polytrimethyl siloxymethacrylate copolymer, acrylates/stearyl acrylate/ ethylamine oxide methacrylate copolymer, acrylates/trifluoropropylmethacrylate/polytrimethyl siloxymethacrylate copolymer, acrylates/VA copolymer, acrylates/VP copolymer, adipic acid/diethylenetriamine copolymer, adipic acid/ dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, amodimethicone/silsesquioxane copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, behenyl methacrylate/ethylamine oxide methacrylate copolymer, bis-butyloxyamodimethicone/PEG-60 copolymer, bis-isobutyl PEG-14/amodimethicone copolymer, bis-isobutyl PEG-15/ amodimethicone copolymer, butyl acrylate/ethylhexyl methacrylate copolymer, butyl acrylate/hydroxypropyl dimethicone acrylate copolymer, butyl ester of ethylene/MA copolymer, butyl ester of PVM/MA copolymer, calcium/ sodium PVM/MA copolymer, chitosan, chitosan lactate, corn starch/acrylamide/sodium acrylate copolymer, dehydroxanthan gum, diethylene glycolamine/epichlorohydrin/ piperazine copolymer, dimethicone crosspolymer, dimethicone/silsesquioxane copolymer, diphenyl amodimethicone, ethyl ester of PVM/MA copolymer, ethyltrimonium chloride methacrylate/hydroxyethylacrylamide copolymer, hydrolyzed wheat protein/PVP crosspolymer, hydroxypropyl dimethiconylpropyl acrylates copolymer, hydroxypropyltrimonium hydrolyzed corn starch, isobutylene/ethylmaleimide/hydroxyethylmaleimide copolymer, isobutylene/MA copolymer, isobutylmethacrylate/trifluoroethylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, lauryl PEG-9 polydimethylsiloxyethyl dimethicone, methacrylic acid/sodium acrylamidomethyl propane sulfonate copolymer, methacryloyl ethyl betaine/acrylates copolymer, methoxy amodimethicone/silsesquioxane copolymer, methoxy PEG-114/polyepsilon caprolactone, myristic/palmitic/stearic/ricinoleic/eicosanedioic glycerides, octylacrylamide/acrylates/butylaminoethyl methacrylate copolymer, PEG-800/polyvinyl alcohol copolymer, PEG/PPG-25/25 dimethicone/acrylates copolymer, PEG-8/ SMDI copolymer, polyacrylamide, polyacrylate-6, polyacrylate-8, polyacrylate-9, polyacrylate-15, polyacrylate-16, polyacrylate-17, polyacrylate-18, polyacrylate-19, polybeta-alanine/glutaric acid crosspolymer, polybutylene terephthalate, polyester-1, polyethylacrylate, polyethylene terephthalate, polyimide-1, polymethacryloyl ethyl betaine, polypentaerythrityl terephthalate, polyperfluoroperhydrophenanthrene, polyquaternium-4/hydroxypropyl starch copolymer, polyurethane-1, polyurethane-6, polyurethane-10, polyurethane-18, polyurethane-19, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PVM/MA copolymer, PVP/VA/itaconic acid copolymer, PVP/VA/vinyl propionate copolymer, rhizobian gum, rosin acrylate, shellac, silicone quaternium-16/glycidoxydimethicone crosspolymer, sodium butyl ester of PVM/ MA copolymer, sodium ethyl ester of PVM/MA copolymer, sodium polyacrylate, sodium polygamma-glutamate, soy protein phthalate, sterculia urens gum, terephthalic acid/ lsophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/ vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/methacrylamide/vinyl imidazole copolymer, VP/VA copolymer, VP/vinyl caprolactam/ DMAPA acrylates copolymer, yeast palmitate, a silicon-based polymer or resin such as phenylpropyldimethyl siloxysilicate, trimethylsiloxysilicate, cyclopentasiloxane, trimethylsiloxysilicate, diisostearoyl trimethyllolpropane siloxy silicate, vinyl dimethicone crosspoylmer/blends, and alkyl cetearyl dimethicone crosspolymers.

In some exemplary embodiments, the foam stabilizer includes a VP/vinylcaprolactam/dimethylaminopropyl methacrylamide copolymer sold under the trade names Aquaflex SF-40, or an isobutylene/dimethylaminopropyl maleimide/ethoxylated maleimide/maleic acid copolymer sold under the trade name Aquaflex XL-30.

In one embodiment, foam stabilizer is present in an amount of from about 0.005 to about 4 weight percent, based upon the total weight of the non-antimicrobial cleansing composition. In another embodiment, the foam stabilizer is present in an amount of from about 0.01 to about 1 weight percent, based upon the total weight of the alcoholic composition, and in yet another embodiment, the foam stabilizer is present in an amount of from about 0.02 to about 0.2 weight percent, based upon the total weight of the non-antimicrobial cleansing composition.

The non-antimicrobial cleansing composition may be formulated as a liquid soap composition, rather than a foam. In such embodiments, the non-antimicrobial cleansing composition would include one or more thickening agents and optionally one or more stabilizers. Examples of thickening agents and stabilizers include polyurethane-based thickeners, such as steareth-100/PEG-136/HDI copolymer (Rheoluxe® 811); sodium chloride; propylene glycol; PEG-120 methyl glucose dioleate and methyl gluceth-10 (Ritathix DOE, available from Rita Corp.); hydroxyethyl cellulose; quaternized hydroxyethyl cellulose (Polyquaternium-10); Poly(2-methacryloxyethyltrimethylammonium chloride) (Polyquaternium-37); polyquaternium-39; hydroxypropyl cellulose; methyl cellulose; carboxymethyl cellulose; starch polymers; guar hydroxypropyltrimonium chloride; and ammonium acryloyldimethyltaurate/VP copolymer.

In one or more exemplary embodiments, the liquid non-antimicrobial cleansing composition may include polyacrylate thickening agents such as those conventionally available and/or known in the art. Examples of polyacrylate thickening agents include carbomers, acrylates/C10-30 alkyl acrylate cross-polymers, copolymers of acrylic acid and alkyl (C5-C10) acrylate, copolymers of acrylic acid and maleic anhydride, and mixtures thereof. In one or more embodiments, the non-antimicrobial cleansing composition includes an effective amount of a polymeric thickening agent to adjust the viscosity of the composition to a viscosity range of from about 1000 to about 65,000 centipoise. In some embodiments, the viscosity of the composition is from about 5,000 to about 35,000, and in another embodiment, the viscosity is from about 10,000 to about 25,000. The viscosity is measured by a Brookfield RV Viscometer using RV and/or LV Spindles at 22° C.+/−3° C.

As will be appreciated by one of skill in the art, the effective amount of thickening agent will vary depending upon a number of factors, including the amount of other ingredients in the non-antimicrobial composition. In one or more embodiments, an effective amount of thickening agent is at least about 0.01 wt. %, based upon the total weight of the composition. In other embodiments, the effective amount is at least about 0.02 wt. %, or at least about 0.05 wt. %, or at least about 0.1 wt. %. In certain exemplary embodiments, the effective amount of thickening agent is at least about 0.5 wt. %, or at least about 0.75 wt. %, based upon the total weight of the composition. In one or more embodiments, the compositions according to the present invention comprise up to about 10% by weight of the total composition of a thickening agent. In certain embodiments, the amount of thickening agent is from about 0.01 to about 1.0 wt. %, or from about 0.02 to about 0.4 wt. %, or from about 0.05 to about 0.3 wt. %, based upon the total weight of the composition. The amount of thickening agent may be from about 0.1 to about 10.0 wt. %, or from about 0.5 to about 5.0 wt. %, or from about 0.75 to about 2.0 wt. %, based upon the total weight of the composition.

Optionally, compositions of the cleansing composition may include one or more pharmacological agents, with the proviso that the pharmacological ingredient does not deleteriously affect the properties of the composition. Examples of such agents include, but are not limited to, antifungal agents, antiviral agents, antimicrobial agents, and antiparasitic agents. In one or more embodiments, one or more antimicrobial agents are included, such that the composition may be characterized as an antimicrobial composition.

Examples of antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis (4-chlorophenyl)-3,12-diimino-2,4,11,14-tetraazatetradecanediimidiamide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 200; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, a blend of hiostatic and fungistatic agents having the INCI name capryihydroxamic acid (and) propanediol, and mixtures thereof.

In one or more embodiments, the composition comprises from about 0.05 to about 3 wt. %, in other embodiments, from about 0.07 to about 2.5 wt. %, in other embodiments, from about 0.09 to about 1 wt. %, in other embodiments, from about 0.1 to about 0.75 wt. %, in other embodiments, from about 0.15 to about 0.5 wt. %, of at least one antimicrobial agents, based upon the total weight of the composition.

In one or more embodiments, compositions of the present invention may further include one or more probiotics and/or prebiotics. In one or more embodiments, the one or more probiotics include one or more skin commensal microorganisms which positively affect the skin microbiota. For example, the one or more probiotics can include microorganisms that positively affect the skin surface environment, e.g., by altering the pH or inhibiting growth of pathogenic microorganisms. In one or more embodiments, the one or more probiotics can include one or more microorganisms naturally found on the skin surface of the individual. In one or more embodiments, the one or more probiotics can include one or more microorganism that are not naturally found on the skin surface of the individual, but positively affect the skin surface environment. In one or more embodiments, the one or more probiotics can include one or more engineered microorganisms. For example, the one or more probiotics can include a microorganism genetically engineered to have a property that positively affects the skin surface environment, e.g., by synthesizing and excreting an inhibitor of pathogenic microorganisms. See e.g., Martin et al. (2013) Microbial Cell Factories, 12:71, which is incorporated herein by reference. In one or more embodiments, the probiotic comprises live probiotic microorganisms. In one or more embodiments, the probiotics may be included in a live form, dead form, semi-active or in deactivated form and fragments or fractions originating from the microorganism either live or dead (e.g., as a lyophilized powder). In one or more embodiments, the probiotic includes culture supernatants of the microorganisms.

In one or more embodiments, the one or more probiotics include one or more bacterial probiotics. In one or more embodiments, the one or more bacterial probiotics include one or more of Firmicutes, Actinobacteria, Bacteriodetes, Proteobacteria, or Cyanobacteria. In one or more embodiments, the one or more bacterial probiotics include one or more of *Corynebacteria, Propionibacteria, Micrococci*, or *Staphylococci*. In one or more embodiments, the one or more bacterial probiotics include non-lactic acid and/or lactic acid producing bacteria (LAB) and can include *Bacteroides, Bifidobacterium*, and *Lactobacillus*. In one or more embodiments, the one or more bacterial probiotics include certain strains of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium*, and *Weissella*. A wide variety of strains of bacteria are available from the ATCC, Manassas, Va. In one or more embodiments, the one or more probiotics include one or more non-pathogenic strains of pathogenic bacteria.

In one or more embodiments, the one or more treatment agents include one or more prebiotics. In one or more embodiments, the one or more prebiotics are agents that promote the survival and/or growth of microorganisms of interest on the skin surface of the individual. In one or more embodiments, the one or more prebiotics include at least one of galacto-oligosaccharides, fructo-oligosaccharides, inulin, or lactulose. In one or more embodiments, the one or more prebiotics include one or more of iron, biotin, nicotinic acid, D-pantothenic acid, pyridoxal, pyridoxamine dihydrochloride, thiamin hydrochloride, valine, arginine, galactose, mannose, fructose, sucrose, lactose, or maltose. In one or more embodiments, the one or more prebiotics include one or more of plant derived prebiotics, e.g., derived from acacia gum, konjac, chicory root, Jerusalem artichoke, asparagus, and dandelion greens. See e.g., U.S. Patent Application Publication NO. 2013/0115317 A1 and Bateni et al. (2013) Am. J. Dermatology Venereology 2:10-14, both of which are incorporated herein by reference.

The composition may further comprise a wide range of optional ingredients that do not deleteriously affect skin health, aesthetics, or foam quality. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

The compositions of the present invention may be employed in many types of dispensers typically used for soaps, sanitizers, or lotion products, for example pump dispensers. In some embodiments, when delivering a concentrate product the pump volumes may need to be adjusted to deliver lower volumes of liquid and/or higher volumes of air (when dispensing foam). A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, 7,611,030, and 7,621,426, all of which are incorporated herein by reference. In one or more embodiments, the dispenser includes an outlet such as a nozzle, through which the composition is dispensed. In certain exemplary embodiments, the non-antimicrobial composition is used in dispensers that employ foaming pumps, which combine ambient air or an inert gas and the composition in a mixing chamber and pass the mixture through a mesh screen. Exemplary embodiments of foam pumps that may be used are shown and described in, U.S. Pat. No. 7,303,099 titled Stepped Pump Foam Dispenser; U.S. Pat. No. 8,002,150 titled Split Engagement Flange for Soap Piston; U.S. Pat. No. 8,091,739 titled Engagement Flange for Fluid Dispenser Pump Piston; U.S. Pat. No. 8,113,388 titled Engagement Flange for Removable Dispenser Cartridge; U.S. Pat. No. 8,272,539, Angled Slot Foam Dispenser; U.S. Pat. No. 8,272,540 titled Split Engagement Flange for Soap Dispenser Pump Piston; U.S. Pat. No. 8,464,912 titled Split Engagement Flange for Soap Dispenser Pump Piston; U.S. Pat. No. 8,360,286 titled Draw Back Push Pump; U.S. patent application Ser. No. 15/429,389 titled High Quality Non-Aerosol Hand Sanitizing Foam; U.S. patent application Ser. No. 15/369,007 Sequentially Activated Multi-Diaphragm Foam Pumps, Refill Units and Dispenser Systems; U.S. Pat. No. 8,172,555 titled Diaphragm Foam Pump; U.S. 2008/0,277,421 titled Gear Pump and Foam Dispenser, all of which are incorporated herein by reference in their entirety.

Exemplary touch-fee dispensers are also shown and described in U.S. Pat. No. 7,837,066 titled Electronically Keyed Dispensing System And Related Methods Utilizing Near Field Response; U.S. Pat. No. 9,172,266 title Power Systems For Touch Free Dispensers and Refill Units Containing a Power Source; U.S. Pat. No. 7,909,209 titled Apparatus for Hands-Free Dispensing of a Measured Quantity of Material; U.S. Pat. No. 7,611,030 titled Apparatus for Hands-Free Dispensing of a Measured Quantity of Material; U.S. Pat. No. 7,621,426 titled Electronically Keyed Dispensing Systems and Related Methods Utilizing Near Field Response; and U.S. Pat. No. 8,960,498 titled Touch-Free Dispenser with Single Cell Operation and Battery Banking; all which are incorporated herein by reference.

Exemplary dispensers and pumps that are particularly suitable for dispensing the compositions disclosed herein in the form of foam may be found in U.S. patent application Ser. No. 15/356,795 titled Foam Dispensing Systems, Pumps and Refill Units Having High Air to Liquid Ratios, and U.S. patent application Ser. No. 15/480,711 titled Sequentially Activated Multi-Diaphragm Foam Pumps, Refill Units and Dispenser Systems, which are incorporated herein by reference in their entirety.

In one or more embodiments, the non-antimicrobial composition is integrated into wipe composition. Suitable wipe substrates are further described in U.S. Pat. Nos. 5,686,088, 6,410,499, 6,436,892, 6,495,508, 6,844,308. In one or more embodiments, the wipe may comprise a laminate formed by spunbonding/meltblowing/spunbonding (SMS). Generally, an SMS material contains a meltblown web sandwiched between two exteriors spunbond webs. SMS materials are further described in U.S. Pat. Nos. 4,041,203, 5,169,706, 5,464,688, and 4,766,029, and are commercially available, for example from Kimberly-Clark Corporation under marks such as Spunguard 7 and Evolution 7. The SMS laminate may be treated or untreated.

In some exemplary embodiments, the non-antimicrobial cleansing composition removes at least 90% of soil and pathogens on a surface, including at least 95%, 97%, 98%, and 99%. According to certain exemplary embodiments, the non-antimicrobial cleansing composition removes 80 to 99.9% of Serratia marcescens bacteria from the surface of the skin, including without limitation, 98.0 to 99.9%, 99.3 to 99.8%, 99.4 to 99.6%, 99.2 to 99.8%, 99.1 to 99.9%, etc. According to certain exemplary embodiments, the non-antimicrobial cleansing composition removes 80 to 99.9% of Staph aureus bacteria from a surface of the skin, including without limitation, 99.4 to 99.7%, 99.3 to 99.6%, 99.2 to 99.8%, 99.1 to 99.9%, etc. Moreover, as illustrated below in Table 1, the non-antimicrobial cleansing composition further demonstrates removal of at least 99% of Enterococcus faecalis bacteria from the skin

TABLE 1

|  | Product | |
| --- | --- | --- |
|  | Non-antimicrobial Cleansing Comp. | Comparable Soap without Alcohol |
| Baseline Inoculum (Log CFU/hand) ± St. Deviation | 7.56 ± 0.32 | 7.28 ± 0.45 |
| Log Reduction (Log CFU/hand) ± St. Deviation | 2.21 ± 0.48 | 1.91 ± 0.46 |
| Percent Reduction | 99.13% | 98.15% |
| N | 9 | 9 |

It has been surprisingly discovered that the non-antimicrobial cleansing composition is effective in the removal of C. difficile spores. According to certain exemplary embodiments, the topical cleansing composition achieves at least a 93% reduction in spores, including without limitation, reductions of at least 93.5%, at least 94%, and at least 94.5%.

Table 2, below, illustrates the comparative results of treating a C. difficile contaminated surface with the cleansing cleaner disclosed herein, compared to an otherwise comparable soap that does not include alcohol. Hands were contaminated with 150 µl spores applied to palmar surface of each hand and rubbed together, including palmar surface of fingers. Test method is consistent with method described in Edmonds et al (2013) Effectiveness of Hand Hygiene for Removal of Clostridium difficile Spores from Hands. ICHE 34, 302-305. As illustrated in Table 2, the non-antimicrobial cleansing composition demonstrates a 1.26±0.26 log reduction in C. difficile spores, compared to a log reduction of only 0.97±0.19 when treated with a comparable soap not containing alcohol.

TABLE 2

|  | Product | |
| --- | --- | --- |
|  | Topical Cleansing Comp. | Comparable Soap without Alcohol "Bland soap" |
| Baseline Inoculum (Log CFU/hand) | 7.98 | 7.97 |
| Log Reduction (Log CFU/hand) ± St. Deviation | 1.26 ± 0.26 | 0.97 ± 0.19 |

It has been surprisingly discovered that although the non-antimicrobial cleansing composition is capable of achieving a high level of pathogen removal, the level of microbial kill remains below 3.5 log. In some exemplary embodiments, the level of microbial kill is not greater than 3.0 log, such as less than or equal to 2.5 log, 2.3 log, 2.1 log, 1.9 log, or 1.5 log. As illustrated in FIG. 1, at an ethanol concentration of 30 wt. %, the level of microbial kill for both S. marcescens and S. aureus is below a 2.0 log kill. At an ethanol concentration of 20 wt. %, the level of microbial kill drops to below a 0.5 log kill.

A surprising benefit of the present non-antimicrobial cleansing composition is that even with the presence of alcohol, the composition does not negatively impact skin's water content after use, as measured by the transepidermal water loss measurement. In some exemplary embodiments, after application to a skin surface, the non-antimicrobial cleansing composition produces a transepidermal water loss measurement that is not higher by a statistically significant amount, compared to an otherwise identical composition that does not include alcohol.

Another benefit of the present non-antimicrobial cleansing composition is that even with the presence of alcohol, the composition improves skin's overall hydration after use, as measured using a Corneometer®. In some exemplary embodiments, the non-antimicrobial cleansing composition produces a hydration level that is not lower by a statistically significant amount, compared to an otherwise identical composition that does not include alcohol.

It has further been discovered that the non-antimicrobial cleansing composition has a reduced interfacial tension on the surface of skin compared to otherwise comparable soaps without the synergistic alcohol and surfactant system, which improves the spreadability of the composition and shortens rinse time. Interfacial tension is the force between the liquid phase of one substance and either the solid, liquid, or gas phase of another substance. The interaction occurs at the surface of each substance, hence, their interface. In the present case, the interfacial tension measures the energy present at the interface of the skin (or other topical surface) and the topical composition. For a soap, a low interfacial tension is indicative of efficient spreading, good coverage of liquid on a surface, better potential to displace dirt from surfaces, and faster rinsing. A low interfacial tension comes from matching the overall surface tension and surface polarity of the liquid to that of the surface to which the soap is being applied.

Figure 2:
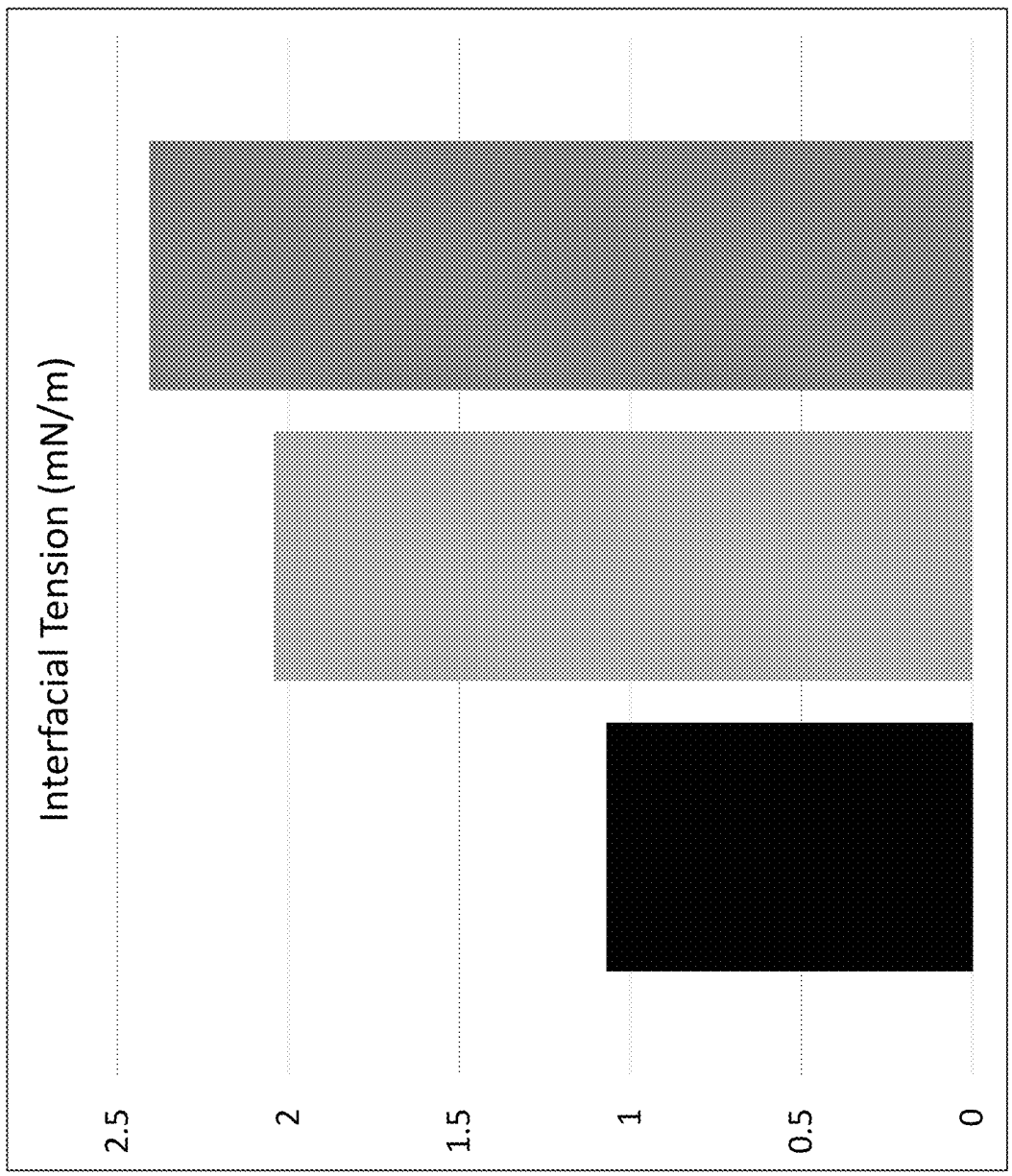
FIG. 2 graphically illustrates the interfacial tension between the surface of skin samples and various non-antimicrobial cleansing compositions.

In some exemplary embodiments, the non-antimicrobial cleansing composition achieves a reduction in interfacial tension by at least 2× that of an otherwise comparable soap that does not include the synergistic alcohol and surfactant system. Such a reduction in interfacial tension is illustrated in FIG. 2, which compares the interfacial tension of the present cleansing composition (Sample A) with that of 1) an otherwise comparable soap that does not include at least 10% alcohol (Comparative Sample 1) and 2) a commercially available non-antimicrobial soap (Comparable Sample 2). As shown in FIG. 2, the interfacial tension of the non-antimicrobial cleansing composition is about 1.15 mN/m, while the interfacial tension of Comparative Sample 1 is about 2.1 mN/m and Comparative Sample 2 is about 2.4 mN/m.

Further improvements to the spreadability of the non-antimicrobial cleansing composition result from the composition's reduced contact angle. The contact angle is a measurement of the angle of incidence between a surface and a liquid. For instance, water has a high contact angle and will sit as a droplet on the skin, while ethanol has a low contact angle and will quickly spread into cracks and crevices on the skin. Lower contact angle means that a formula has superior wetting and spreading on skin.

In some exemplary embodiments, the non-antimicrobial cleansing composition has a contact angle of less than 30° after 1 second of application to the surface of skin and a contact angle of less than 10° after 2 seconds of application to the surface of the skin. In other exemplary embodiments, the non-antimicrobial cleansing composition has a contact angle of less than 20° after 1 second of application to the surface of skin and a contact angle of less than 5° after 2 seconds of application to the surface of the skin.

Figure 3:
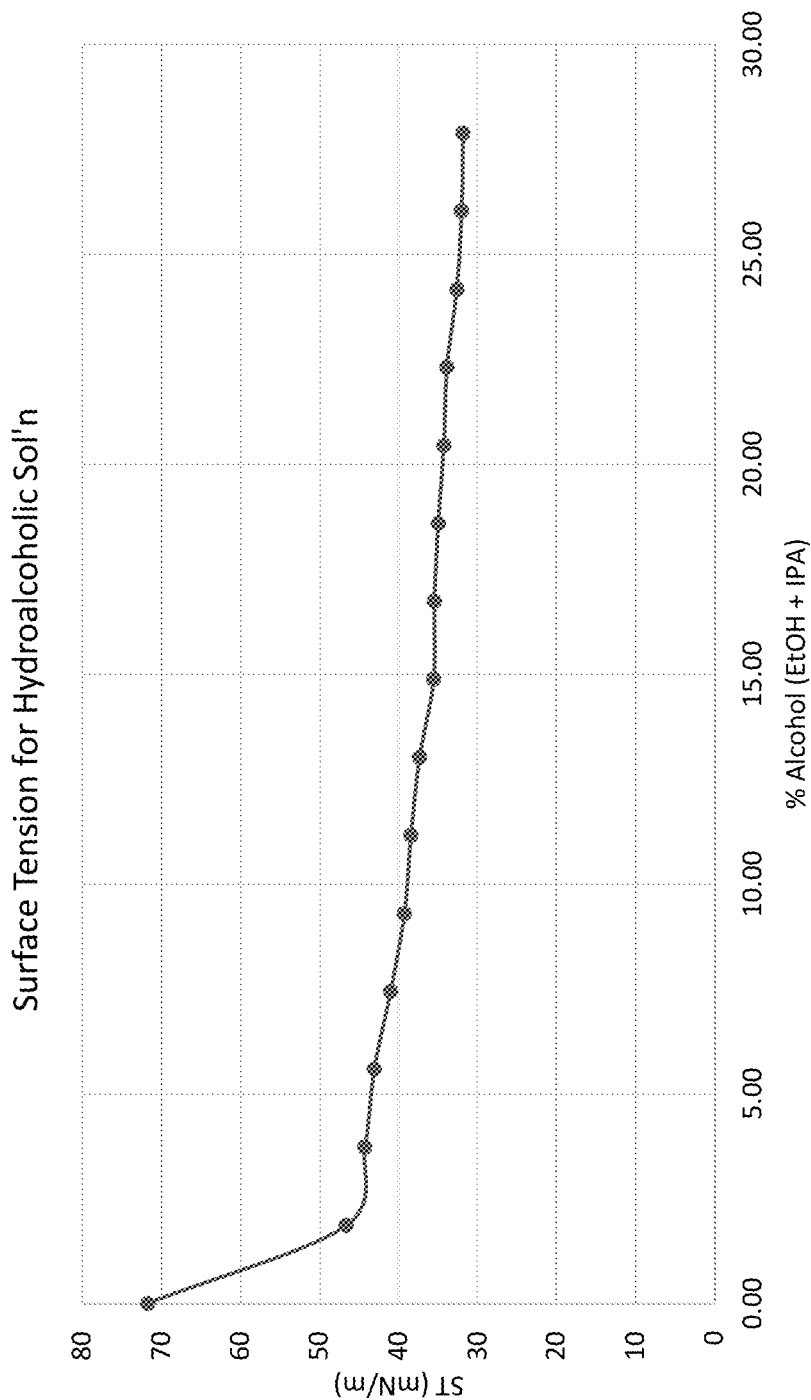
FIG. 3 graphically illustrates the surface tension of hydroalcoholic solutions at various concentrations of alcohol.
Figure 4:
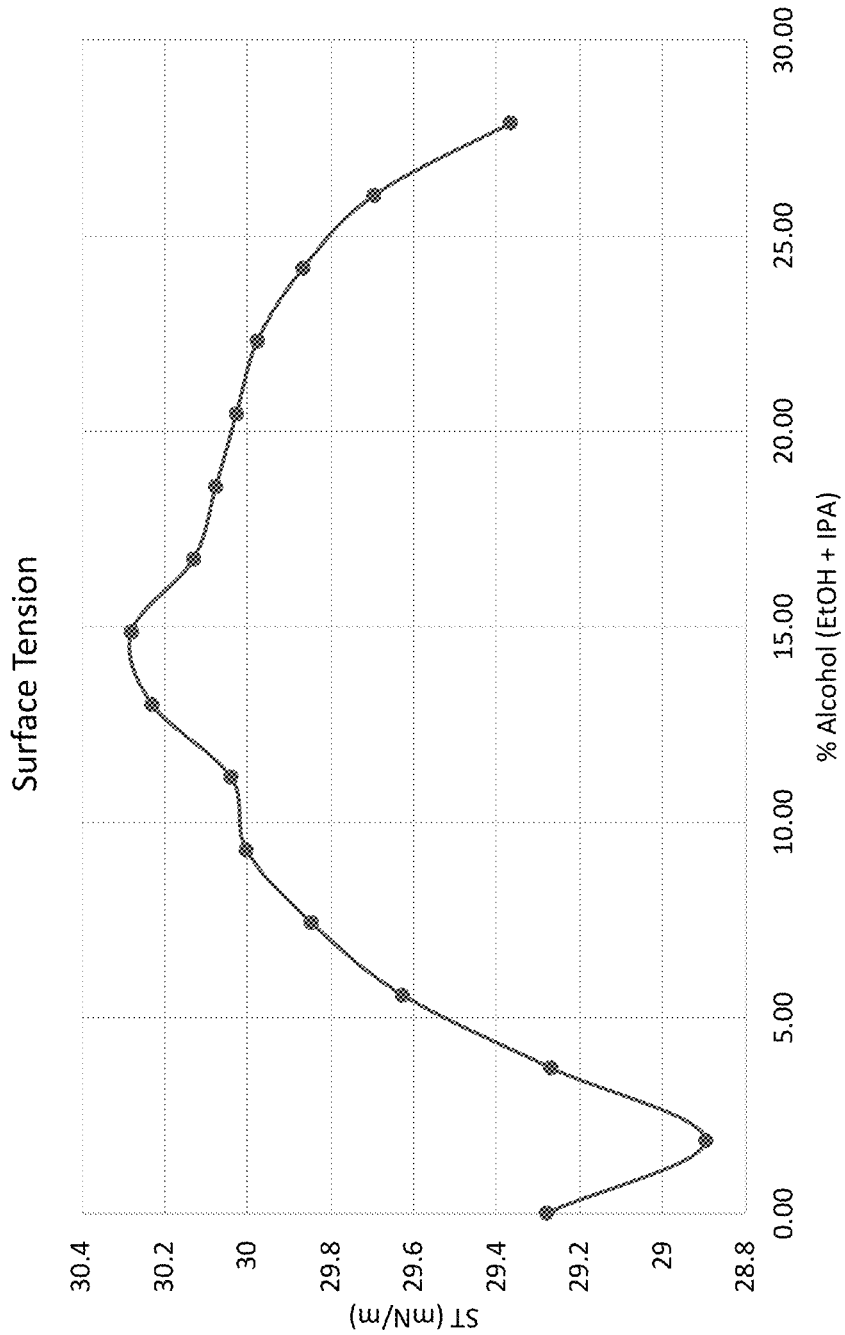
FIG. 4 graphically illustrates the surface tension of the non-antimicrobial cleansing composition at various concentrations of alcohol.

It was additionally surprising to discover that although the presence of alcohol typically reduces the surface tension in hydroalcoholic solutions (See, FIG. 3), the surface tension of the present composition actually increased as the concentration of alcohol was increased from about 2 wt. % to about 28 wt. % (See, FIG. 4). In some exemplary embodiments, the composition has a surface tension between about 29.6 mN/m and about 30.3 mN/m.

In some exemplary embodiments, the non-antimicrobial cleansing composition includes the following:

TABLE 3

| Ingredient | Wt. % |
| --- | --- |
| $C_1$—$C_8$ Alcohol | 10.0-30.0 |
| Primary Surfactant(s) | 2.0-10.0 |
| Secondary Surfactant(s) | 0-8.0 |
| Humectant | 0.25-5.0 |
| Emollient | 0.1-2.0 |
| pH adjuster | 0.01-1.0 |
| Water | q.s |

TABLE 4

| Ingredient | Wt. % |
| --- | --- |
| $C_1$—$C_8$ Alcohol | 15.0-25.0 |
| Primary Surfactant(s) | 2.5-5.0 |
| Secondary Surfactant(s) | 2.0-5.0 |
| Humectant | 1.0-3.5 |
| Emollient | 0.15-1.0 |
| pH adjuster | 0.025-0.075 |
| Water | q.s |

TABLE 5

| Ingredient | Wt. % |
| --- | --- |
| $C_1$—$C_8$ Alcohol | 15.0-30 |
| Fatty acid | 3.0-8.0 |
| Humectant | 0.5-3.0 |
| Emollient | 0.15-1.0 |
| pH adjuster (basic) | 2.0-8.0 |
| Antioxidant | 0-1.0 |
| Water | q.s. |

Further exemplary embodiments relate to a method of skin treatment for removing pathogens and controlling transepidermal water loss (TWEL). In certain exemplary embodiments, the method includes applying a non-antimicrobial cleansing composition to a skin surface. In certain exemplary embodiments, the non-antimicrobial composition includes from about 10 to about 40 wt. % of one or more $C_1$-$C_8$ alcohols based on the total weight of the composition; at least about 5 wt. % of one or more surfactants; and water.

In certain exemplary embodiments, the method results in the non-antimicrobial cleansing composition removing at least 99% of soil and pathogens. In certain exemplary embodiments, the method further includes rinsing the non-antimicrobial cleansing composition off of the surface with water. In certain exemplary embodiments, the 80 to 99% of Serratia marcescens bacteria is removed from a surface of the skin upon using the method.

EXAMPLES

The following examples are included for purposes of illustration and are not intended to limit the scope of the disclosure described herein.

Example 1

Topical compositions were tested on skin samples for their ability to improve or maintain skin hydration and limit transepidermal water loss (TEWL). Measurement of the TEWL, expressed in grams per square meter and per hour, is used for studying the water barrier function of the human skin. The more perfect the skin protective coat, the higher the water content and the lower the TEWL. For each of the tests, a negative control was used, which included treatment with 8% SLS. An untreated skin sample was also tested for comparison. The tests were performed using the forearm controlled application test (FCAT) methodology. The various samples were applied to test sites on a forearm over the course of several days. On each day, up to six applications were made and the change in TEWL and hydration levels were recorded. The hydration levels were measured using a Corneometer® based on capacitance measurement of a dielectric medium. The Corneometer® measures the change in the dielectric constant due to skin surface hydration changing the capacitance of a precision capacitor. The measurement can detect even slight changes in the hydration level.

The change in TEWL and hydration levels represent the change observed for that particular sample compared to a baseline (the transepidermal water content or hydration level prior to treatment). It was expected that the untreated sample would demonstrated the highest hydration levels and the lowest TEWL. Similarly, the negative control was expected to have the lowest hydration levels and the highest TEWL, since SLS is known to be a skin irritant and dissolves the natural oils on skin, causing a drying effect. The compositions that were tested include the following, in weight %, based on the weight of the total composition:

TABLE 9

|  | Control A | Sample 1 | Sample 2 |
|---|---|---|---|
| SDA 3C Alcohol (88.1% EtOH) | 0 | 15 | 30 |
| Sodium laureth sulfate | 2.45 | 2.45 | 2.45 |
| Citric acid | 0.05 | 0.05 | 0.05 |
| Cocamidopropyl betaine and disodium cocoamphodiacetate | 1.20 | 1.20 | 1.20 |
| Glycerin and PEG-8 and sodium PCA | 2.5 | 2.5 | 2.5 |
| PEG-7 glyceryl cocoate | 0.25 | 0.25 | 0.25 |
| Polyquaternium-39 | 0.2 | 0.2 | 0.2 |
| Sodium metabisulfite | 0.1 | 0.1 | 0.1 |
| Trisodium EDDS | 0.3 | 0.3 | 0.3 |
| Water | q.s. | q.s. | q.s. |

TABLE 10

|  | Control B | Sample 3 | Sample 4 |
|---|---|---|---|
| SDA 3C Alcohol (88.1% EtOH) | 0 | 15 | 30 |
| Lauric acid | 5.0 | 5.0 | 5.0 |
| Poloxamer 124 | 1.0 | 1.0 | 1.0 |
| Dipropylene glycol | 3.0 | 3.0 | 3.0 |
| pH adjuster (Monoethanolamine, lactic acid) | 6.56 | 6.56 | 6.56 |
| Glycerin | 1.75 | 1.75 | 1.75 |
| Sodium PCA | 0.25 | 0.25 | 0.25 |
| Sodium metabisulfite | 0.1 | 0.1 | 0.1 |
| Trisodium EDDS | 0.3 | 0.3 | 0.3 |
| Water | q.s. | q.s. | q.s. |

Figure 5:
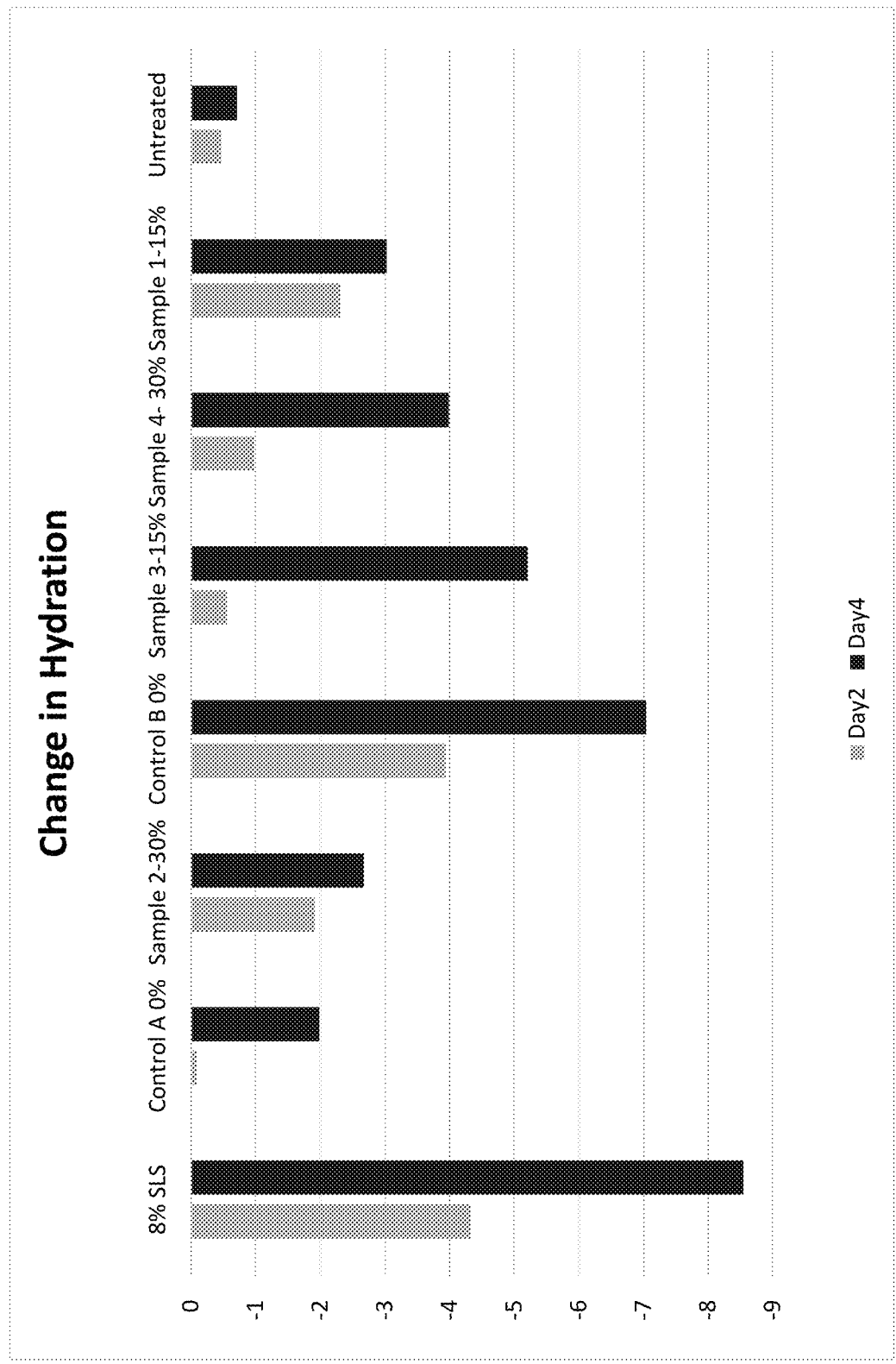
FIG. 5 graphically illustrates the change in skin hydration of skin samples after treatment with various non-antimicrobial cleansing compositions.

As illustrated in FIG. 5, the negative control indeed demonstrated the lowest hydration levels. Similarly, Control B with 0% alcohol demonstrated hydrations levels at days 2 and 4 that are comparable to the negative control. However, with the addition of alcohol, Samples 3 and 4 demonstrated improved hydration levels, with day two levels comparable to the untreated skin sample. Additionally, Samples 1 and 2 demonstrated comparable hydration levels to the control, with the differences in measured hydration levels not being statistically significant. Accordingly, it can be seen that the addition of alcohol to the cleansing compositions did not significantly impair, and in some instances improved, the overall hydration levels of skin after application.

Figure 6:
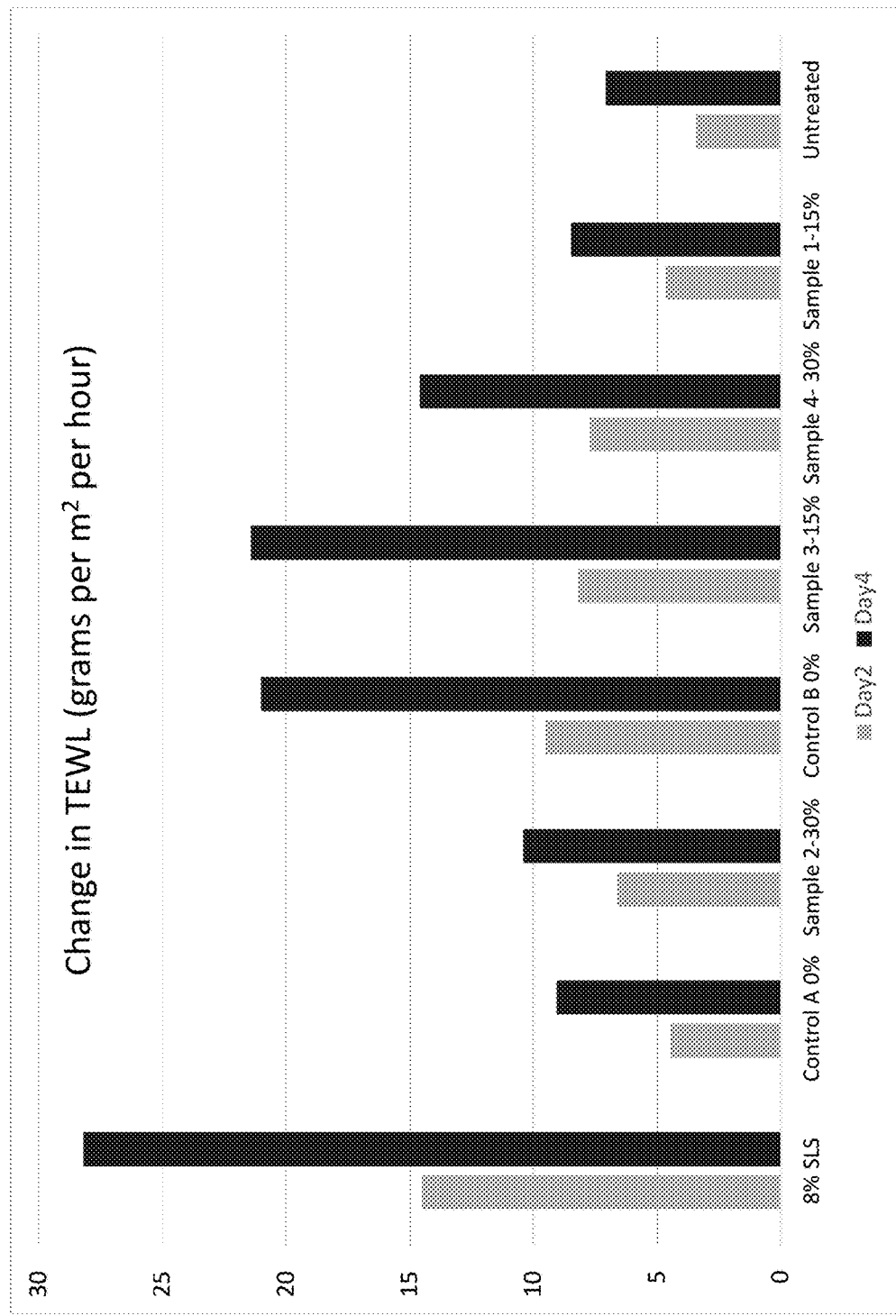
FIG. 6 graphically illustrates the transepidermal water loss of skin samples after treatment with various non-antimicrobial cleansing compositions.

As illustrated in FIG. 6, the negative control indeed demonstrated the highest TEWL. Additionally, Samples 1 and 2 (including 15% and 30% alcohol, respectively), showed markedly less TEWL than the negative control, similar to Control A, which is free of alcohol. This is surprising as alcohol is a known drying agent and would be expected to cause increased water loss. Even more surprising was the reduction in TEWL in Sample 4 (30% alcohol) compared to Control B (0% alcohol).

Example 2

A non-antimicrobial cleansing composition (Sample 5, identical to Samples 1 and 2 above, but with 20% alcohol) was tested for its ability to improve or maintain skin hydration and limit transepidermal water loss, as compared to a negative control containing 8% SLS, untreated skin, and Control A. The samples were tested on both dry and wet skin.

Figure 7:
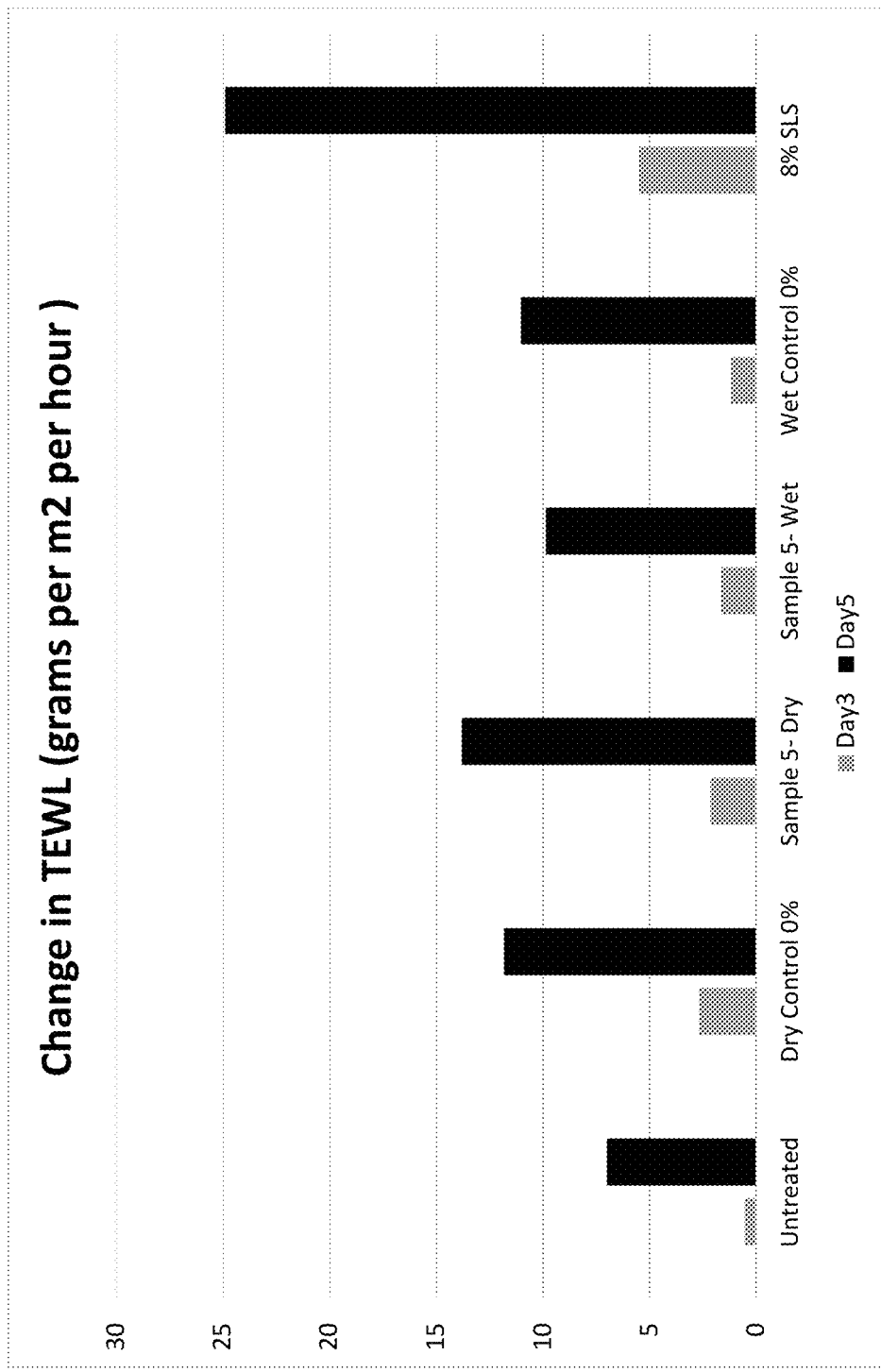
FIG. 7 graphically illustrates the change in skin hydration of skin samples after treatment with various non-antimicrobial cleansing compositions.

FIG. 7 illustrates the change in TEWL observed after treating skin samples with the various compositions. The change in TEWL represents the change observed for that particular sample compared to a baseline (the transepidermal water content prior to treatment). As each composition was applied to a different skin sample, each baseline is different. As illustrated in FIG. 7, the negative control demonstrated significant TEWL, particularly on day 5. In contrast, Sample 5 (both wet and dry application) demonstrated significantly less TEWL after both 3 and 5 days of treatment. The differences between wet and dry application did not appear to be statistically significant.

Figure 8:
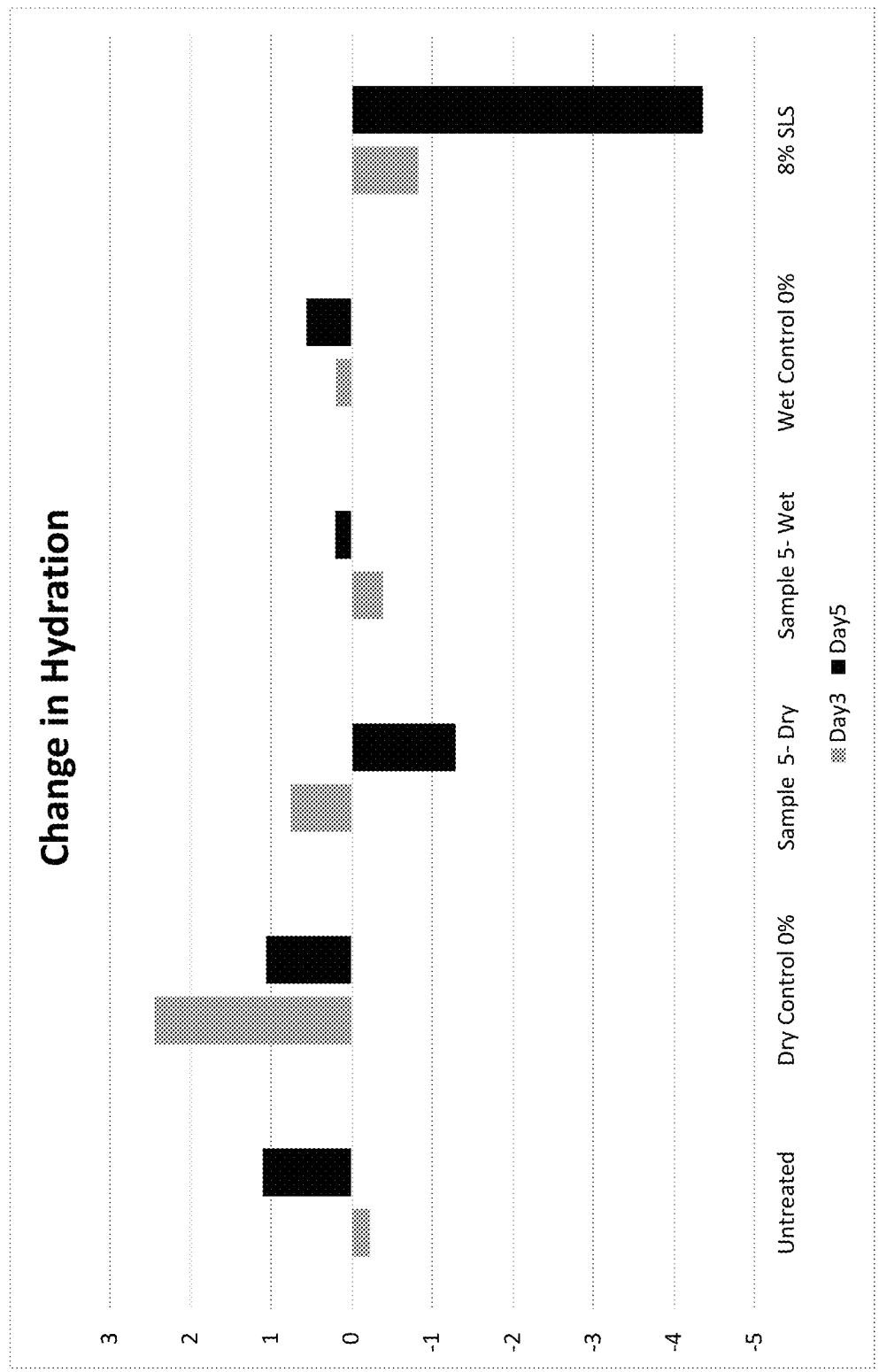
FIG. 8 graphically illustrates the transepidermal water loss of skin samples after treatment with various non-antimicrobial cleansing compositions.

FIG. 8 illustrates the change in hydration levels observed after treating skin samples with the various compositions. The change in hydration levels represents the change observed for that particular sample compared to a baseline (the hydration level prior to treatment). As each composition was applied to a different skin location, each baseline is different. As illustrated in FIG. 8, the negative control demonstrated a significant reduction in hydration level, particularly on day 5. In contrast, Sample 5 (both wet and dry application) demonstrated significantly less hydration loss after both 3 and 5 days of treatment.

Example 3

The non-antimicrobial compositions detailed in Tables 9 and 10, above, were tested for their efficacy in removing *Serratia marcescens* from human skin. Two additional compositions were tested: Sample 6 (identical to Samples 1 and 2, only with 25 wt. % $C_1$-$C_8$ alcohol) and Sample 7 (identical to Samples 3 and 4, only with 25 wt. % $C_1$-$C_8$ alcohol). As illustrated below, in Table 11, each sample tested, including at least 15 wt. % alcohol, removed at least 98% *Serratia marcescens* from human skin.

TABLE 11

| Sample ID | Sample 1 | Sample 6 | Sample 2 | Sample 3 | Sample 7 | Sample 4 |
|---|---|---|---|---|---|---|
| Efficacy (in vivo), *Serratia marcescens* | 99.3% | 99.4% | 99.5% | 98.72% | N/A | 99.8% |

Example 4: Contact Angle and Spreading on Skin

The time resolved contact angle for drops of the non-antimicrobial cleansing composition was tested by placing five drops of three different soap formulations on synthetic skin. The samples were as follows: 1) Sample A: the non-antimicrobial cleansing composition in accordance with the present application; 2) Comparable Sample 1: an otherwise comparable cleansing composition that does not include alcohol; and 3) Comparable Sample 2: a commercial blansoap. Five drops of each of the formulations were placed onto the surface of the synthetic skin and the time resolved contact angle was measured and illustrated in FIG. 9.

Figure 9:
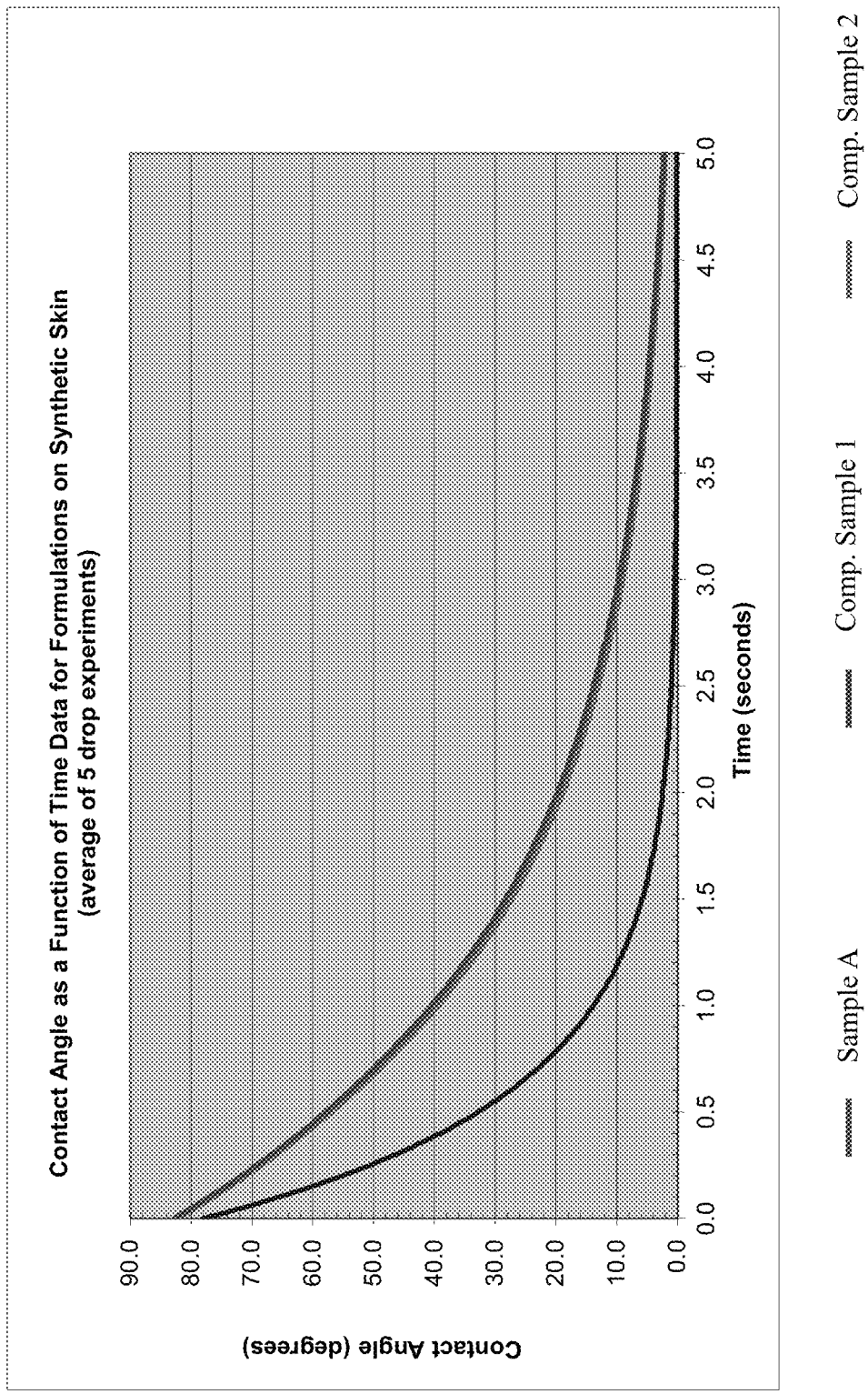
FIG. 9 graphically illustrates the contact angles of various non-antimicrobial cleansing compositions as a function of time.
Figure 10:
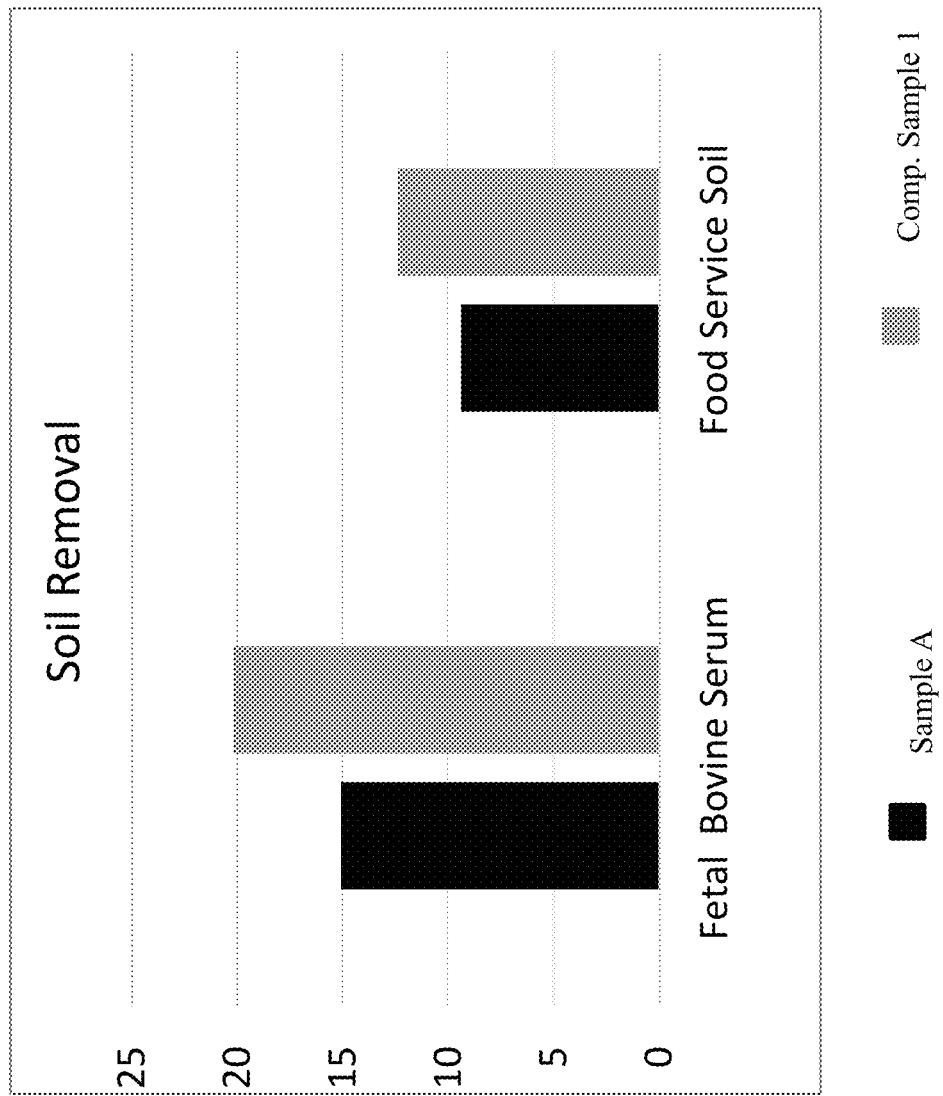
FIG. 10 graphically illustrates the quantitative removal of soil by various non-antimicrobial cleansing compositions.

As shown in FIG. 9, Sample A demonstrated a quick decline in surface tension and was near zero after two seconds of application. In contrast, both Comparable Samples 1 and 2 each demonstrated contact angles of about 20° after two seconds of application. Additionally, Sample A demonstrated a reduction in contact angle from almost 80° at the time of application (t=0) to 10° in 1.2 seconds. In contrast, both Comparative Samples 1 and 2 required 3 seconds for the same reduction in contact angle (from about 80° to 10°).

Example 5: Soil Removal

A tensiometer was used to test quantitative removal of soil. A probe was wrapped with synthetic skin and coated with one of two types of soil: 1) fetal bovine serum for healthcare; and 2) food service soil (Crisco, flour, oil). For this test, the quick dip method was used, in which the coated probe was dipped into one of two cleansing compositions: 1) Sample A: a non-antimicrobial cleansing composition in accordance with the present application; or 2) Comparable Sample 1: an otherwise comparable cleansing composition that does not include alcohol. As illustrated in FIG. 8, Sample A removed 34% more fetal bovine serum and 31% more food service soil. These results indicate that the non-antimicrobial cleansing composition of the present application will remove higher levels of soil than comparable products that do not include the synergistic alcohol and surfactant system.

Example 6

The non-antimicrobial compositions of the present inventive concepts having 20 wt. % alcohol were tested for their antimicrobial activity according to ASTM E2315. Samples of the compositions were inoculated with suspensions of the test organisms. At the exposure time, aliquots were removed, neutralized in BPB+ and plated onto TSA agar to be quantitatively assayed for surviving test organisms. Plates were incubated for 24 hours and the bacterial survivors were enumerated. Results were converted into login format and compared to an initial starting population to determine log reduction.

As illustrated below, in Table 12, the samples tested demonstrated an average of 1.84 log reduction of *Staphylococcus aureus* and less than 1.11 log reduction of *Serratia marcescens*.

TABLE 12

| Sample ID | Log reduction (CFU/mL) |
| --- | --- |
| Efficacy *Staphylococcus aureus* | 1.84 |
| Efficacy *Serratia marcescens* | <1.11 |

Although embodiments of the invention have been described herein, it should be appreciated that many modifications can be made without departing from the spirit and scope of the general inventive concepts. All such modifications are intended to be included within the scope of the invention.

The invention claimed is:

1. A non-antimicrobial cleansing composition comprising:
   from 15 wt. % to 25 wt. % of one or more $C_1$-$C_8$ alcohols;
   a surfactant system comprising from 0.5 wt. % to 5 wt. % of at least one anionic surfactant and from 0.5 wt. % to 5 wt. % collectively of two or more zwitterionic surfactants, wherein the composition is devoid of surfactants comprising sulfate salts with amine-containing counter ions;
   a pH adjusting agent; and
   water, the amounts being based on the total weight of the non-antimicrobial cleansing composition,
   wherein the composition does not achieve a microbial kill level greater than 2.0 log and
   wherein the non-antimicrobial cleansing composition contains less than 10 wt. % of total surfactants.

2. The non-antimicrobial cleansing composition of claim 1, wherein the composition does not achieve a microbial kill level greater than 1.5 log.

3. The non-antimicrobial cleansing composition of claim 1, wherein the one or more $C_1$-$C_8$ alcohols are selected from the group consisting of methanol, ethanol, isopropanol, butanol, pentanol, hexanol, and isomers and mixtures thereof.

4. The non-antimicrobial cleansing composition of claim 1, wherein the one or more $C_1$-$C_8$ alcohols comprise ethanol, isopropanol, or combinations thereof.

5. The non-antimicrobial cleansing composition of claim 1, wherein the composition is a single-phase solution.

6. The non-antimicrobial cleansing composition of claim 1, wherein the at least one anionic surfactant comprises sodium laureth sulfate.

7. The non-antimicrobial cleansing composition of claim 1, wherein the two or more zwitterionic surfactants comprise cocamidopropyl betaine, cocamidopropyl hydroxyl sultaine, lauramidopropyl hydroxyl sultaine, lauramine oxide, myristamine oxide, disodium lauroamphodiacetate, disodium cocoamphodiacetate, sodium lauroamphoacetate, sodium cocoamphoacetate, disodium cocoamphodipropionate, disodium lauroamphodipropionate, or combinations thereof.

8. The non-antimicrobial cleansing composition of claim 1, further comprising from 0.01 wt. % to 5 wt. % of one or more humectants, based on the total weight of the composition.

9. The non-antimicrobial cleansing composition of claim 8, wherein the one or more humectants are selected from the group consisting of propylene glycol, hexylene glycol, 1,4-dihydroxyhexane, 1,2,6-hexanetriol, sorbitol, butylene glycol, caprylyl glycol, methyl propane diol, dipropylene glycol, triethylene glycol, glycerin, polyethylene glycol, ethoxydiglycol, polyethylene sorbitol, and combinations thereof.

10. A method of cleansing a surface comprising:
    applying the non-antimicrobial cleansing composition of claim 1 to the surface.

11. The non-antimicrobial cleansing composition of claim 1, wherein the composition comprises from 0.01 wt. % to 1.0 wt. % of the pH adjusting agent.

12. A cleansing composition comprising:
    from greater than 10 wt. % to less than 40 wt. % of one or more $C_1$-$C_8$ alcohols;
    a pH adjusting agent in an amount up to 1 wt. %;
    from 0.5 wt. % to less than 10 wt. % of a mixture of surfactants, wherein the mixture of surfactants comprises:
      one or more anionic surfactants; and
      two or more amphoteric surfactants,
    wherein the concentrations are based on the total weight of the cleansing composition, and
    wherein the composition is devoid of surfactants comprising sulfate salts with amine-containing counter ions.

13. The cleansing composition of claim 12, wherein the composition is a non-antimicrobial cleansing composition.

14. The cleansing composition of claim 12, wherein the amphoteric surfactants consist of zwitterionic surfactants selected from the group consisting of betaines, sultaines, amphoacetates, amphodiacetates, or combinations thereof.

15. The cleansing composition of claim 12, wherein the one or more anionic surfactants comprise sodium laureth sulfate.

\* \* \* \* \*